United States Patent [19]

States et al.

[11] Patent Number: 5,180,666

[45] Date of Patent: Jan. 19, 1993

[54] METHOD AND CELL LINE FOR TESTING MUTAGENICITY OF A CHEMICAL

[75] Inventors: J. Christopher States, Royal Oak; Ronald N. Hines; Raymond F. Novak, both of West Bloomfield, all of Mich.

[73] Assignee: Wayne State University, Detroit, Mich.

[21] Appl. No.: 721,775

[22] Filed: Jun. 27, 1991

[51] Int. Cl.[5] .................. C12Q 1/02; C12N 5/22; C12N 15/12; C12N 15/09
[52] U.S. Cl. .................. 435/29; 435/172.3; 435/240.2
[58] Field of Search ............ 435/7.23, 240.2, 29, 435/172.3, 7.21; 536/27

[56] References Cited

U.S. PATENT DOCUMENTS 4,696,898  9/1987  Fitts et al. ............ 435/69.3

OTHER PUBLICATIONS

Dogra et al., *Mol. Pharmacol.* vol. 37, 1990, pp. 608–613.
Crespi et al., *Carcinogenesis* vol. 10, 1989, pp. 295–301.
Kraemer et al., *PNAS*, vol. 72, 1975, pp. 59–63.
Govan et al., *NAR*, vol. 18, 1990, pp. 3823–3830.
Hoy et al., *Chem. Abstr.* vol. 102, 1985, abstract No. 19335.

*Primary Examiner*—Richard A. Schwartz
*Assistant Examiner*—James Ketter
*Attorney, Agent, or Firm*—Reising, Ethington, Barnard, Perry & Milton

[57] ABSTRACT

A method of testing the mutagenicity of a chemical includes the steps of exposing test cells to the chemical in vitro, intracellularly metabolizing the chemical into a mutagenic or cytotoxic metabolite and then detecting gene/protein/cell damage in the test cells as an indication of the mutagenicity/cytotoxicity of the chemical.

A cell line is provided for testing mutagenicity of the chemicals, the cell line consisting essentially of fibroblasts normally having no detectable cytochrome P450 mixed function oxidase enzyme activity. The fibroblasts are transformed with chimeric gene constructs containing cytochrome P450 coding sequences and have intracellular cytochrome P450 oxidative metabolizing activity.

15 Claims, 10 Drawing Sheets

Fig-3A pRNH 127 SEQUENCE

```
   1 GCGCCCAATA CGCAAACCGC CTCTCCCCGC GCGTTGGCCG ATTCATTAAT GCAGCTGGCA
  61 CGACAGGTTT CCCGACTGGA AAGCGGGCAG TGAGCGCAAC GCAATTAATG TGAGTTAGCT
 121 CACTCATTAG GCACCCCAGG CTTTACACTT TATGCTTCCG GCTCGTATGT TGTGTGGAAT
 181 TGTGAGCGGA TAACAATTTC ACACAGGAAA CAGCTATGAC CATGATTACG AATTCGACAA
 241 ACATTAAAAA TAGACATTTT ATTACAAGAG TGTAGAGAAG GGAGACCAAT AGAAGGTAAT
 301 TGAAATACCC CCCCTCACT CCAGCCCTAG TCCTGGTGCC TGGATATGTG CACTCCCTGT
 361 GCGCTCTGAT CCCCGCAGAC ACAAGTCCCC AGCCCCTCCA GGACAGCAAT AAGGGTCTTA
 421 CAAGGCCAGA AGGCAGCCCT GTTTGTTCCT GCCTGCAGGA AGGGCAGAGG AATGTGATGT
 481 TCCCAGGAAC TGTGTCCTAG ACCCATAGGG TCAGATTGCT CAGCCTAGTT CAAGCAGTGA
 541 GACTACCTCT GTGCCAGTAT CCTGGGCTGT CTCTTCCCTT CACTCTTGGC AGCTCCCAAT
 601 TGTCAAAGAT TGGACAGGGT CCTGGTTTGG CTAGTTCTAA CTTGCTGAAG CCAGTCAGCA
 661 CCCTCACAGA GCCAGCTAGG TACTGGGCCC AGGGGCTTCC AGAGAGTTCT TCAGAGCTTC
 721 TCAGAGGCCT AAGGACCTCC TAACCCTAGC AGGCCTCCTG GCTCAAGCAC AACTTGGGAA
 781 GGCTCCATCA GCATCTATGT GGCCCTGTTT TACCTGTTGT CTCTGGAGGG TGTGCAGAGG
 841 CAAGTCCAGG GTAGGGCAG TTAGGCTTGC CCACAGCCCA GATAGCAAAA
 901 CTGCAGCCAG ATCAGTGTCT ATGAGTTTCA GGCTGAATCT TAGACCACAT AGGCCAGCCT
 961 GCTGGTCTGG CTGCCCAACC AGACCAGGTA GACAGAGTCT AGGCCCTCAG GCTCTCAAGC
1021 ACCTAAGAGC GCAGCTGCAT TTGGAAGTGC TCACAGCGCC CATGCTTCAT GGTTAGCCCA
1081 TAGATGGGGG TCATGTCCAC CTTCACGCCC AGTGGCACGC TGAATTCCAC CCGTTGCAGC
1141 AGGATAGCCA GGAAGAGAAA GACCTCCCAG CGGGCAATGG TCTCACCGAT ACACTTCCGC
1201 TTGCCCATGC CAAAGATAAT CACCTTCTCA CTTAACACCT TGTCGATAGC ACCATCAGGG
1261 GTGAAAACC GTTCAGGTAG GAACTCAGAT GGGTTGACCC AGAAGTGTCA GTAGCTTCCT GTAACCAGAG
1321 GGAGACAGCT GAAGTGGCAG TTCAGGGCTC AGAAGTGTCA AGTGAGTGGA GCTCCAGCCC
1381 CAAAGGATAG AGGACAGGCA AGCAGCCCAT GGACAGGAGG ATCAATGCAA TGATTGTATT
1441 AATCATATAT AAGAGCTTAA GAGGGTGGAC CCAGCCCTTC CTCTGCATCT CTGAACTTAC
1501 TGGTCATGGT TGATCTGTCA CTGGTTTACA AAGACACAAC GCCCCTTGGG GATGTAAAAG
1561 CCTTTCAAAC TTGTGTCTCT TGTTGTGCTA GGGAGAAAGG AAGCTCAGTC AGGCTCAGGG
1621 CAACAGGCAA ATCTCCCTGT CTCCCATGCC GTGTCCCTCC CACTAACCCT AATCAGGTAT
1681 GTGGTCCGGA GTAAGATCAG TAACAGACAG CAGTGGCTCC ATGGGCCTT ACCTGTGGGG
1741 GATGTGAAG GGGACGAAGG AAGAGTGTCG GAAGGTCTCC AGGATGAAGG CCTCCATATA
1801 GGGCAGATGG GATCTGTCAG AGAGCCGGG CCGCCGTGAC CTGCCAATCA CTGTGTCTGC
1861 AGAACACAGG GACAAGATGG ATGCAGGGGC TGCCTAGACC TGGCAGACC CCTGGCACTG
1921 ACCCCTTTGA AGGGAGCCAC TACCTACCTA GCTCCAGG GCCTCCTCTG TGTACCCTGG
1981 GGTTCATCAC CAAATACATC AGGCTCCAGG AGATAGCAGT TGTGACTGTG TCAAACCCTG
2041 GACAGGGTAG AACAGAACAA GTTAGGCAGG CAGCACAGG TGAGCACT TGAGCACAGG
```

Fig-3B

```
2101 AAGGACACAA TGGGTAACC  ATACCAGCTC CAAGAGGGTC CAAGACGATG TTAATGATCT
2161 TCTCATCTGA CAGCTGGACA TTGGCGTTCT CATCCAGCTG CTTCTGCTCA CAGTGCTCAA
2221 TCAGGCTGTC TGTGATGTCC CGGATGTGGC CCTTAGGTAG GGAAAGTCCA CAGGTGAGCA
2281 AGATCTCAAA CCCAGAGCTA CCTCTCCATC CAGGTCTGGT CCTTCACTAT TCCTAGCACA
2341 TTTGTTCTGG AGGTGATGCC CCTGAGGCT  GTGTCCCAG  CTTCTCTCTG CCTCTGCAAG
2401 GCTCTCTCCT ACTACCTTAG AATGCTGCTA GCCCCAACTC ATGGACATT  TGACACACAG
2461 CGTCTTGTAC TGTTATCATC TGGATGTGCT CTTTATCTTC TTTCTATTAT GAGGCAGGA
2521 GATGAACTCT TTAACTCTTC CTGGCTCCCT CAGCAACTGC CCCAGGGTCC TGCATGTAAT
2581 GACTCTTCAG TGGCTATTGC TGTCTGTGGA AGCATGGAAG GGTTAGTCAA GATAAAGTTC
2641 TATTTCCCTG CCAAGGAAGA AGACTATTCC ACAACTGGCT TCAAGATCCC AGGTTGAAGC
2701 CTTCCTGAGA ACTTGCCAAG CCCCATGCAG TTCCTCTTAC CTTTGACCTC CCAGGCCCTG
2761 ATGCCATCTG CTTCCCACCA CCCACCTGCC CCACCTGCC  CTGTACCTTC TCAAAGGTTT
2821 TGTAGTGCTC CTTGACCATC TTCTGCATGA AGCTGTAGAA CTTCTCATTC AGGTCCTTGA
2881 AGGCATTCAG GGAAGGGTTG GGTAGGTAGC GAAGAATAGG GATGAAGTCA GCTGGGTTTC
2941 CAGAGCCAAC CACCTCCCCG AATTATTAT  TCAGGTTGAC TAGGCTAAGC AGTTCTTGGT
3001 GGTTGTGGTC ATAGCGCCGG CCAAAGCAAA TGGCACAGAT GACATTGGTC ACTGATACCA
3061 CCACATACCT GTAGGGGTTA AGTGCCCAG  GCCCTGCCAT CAGCTCCTGC AACGTGCTTA
3121 TCAGGACCTC AGCCTCCTTG CTCACATGCT CTTCCAGGTA GCCCTGAGGTT GAGGAGGCTG
3181 GGTCAGAGGC AATGGAGAAA CTTTTCAGGC CATTCTGGGC CAGGCGCCGG CGGGCAGCCC
3241 ACACTGGTCC AGAGTCTGGG CTGAAGGACA TGCTCTGACC ATTACTGATG AGGGTGAAGG
3301 TGTAGAGGTC GGGCCGGAGCC GGGCCCGCCG CGCCCTGCCG CACCAGGGCC TGCCGGATGG
3361 TGTCCAGGCC GCTCAGCACC ACCACGGGTG TGGAGCCAAT TCGGATCTGC AGCACGTCCC
3421 CATACTGCTG GCTCATCCTT GACAGTGCCA GGTGCGGGTT CTTTCCCAGG GTCAGCATGT
3481 GCCCAATCAG AGGCCAGCCC CATGGCCGTC GTGTAGGAT  CAGGCCTTTG GGGACCTGAG
3541 GTCTTGAGGC CCTGATTACC CAGAATACCA TGATCTGGTG GACAGAGGCC AGAAGAAACT
3601 CCGTGGCCGA CATGAGATT  GGGAAAAGCA TGATCTGGTG AAGCTGGAGC TACGGAGTAA
3661 GTGAGGAGAA GGTACTCAGG ACGTTGAAGT CGTGGTGACG CTTAGAGGAC AGCCTGCCCT
3721 CTTTATAGTC GTTGGACGAG TCCGGGCGCA AGGGTTTGC  ACCCAGCAGG CGGTTGCTCC
3781 AGCCCACGCA TAGTCACGCG CCCCGGAGCG TGGCAGAGCC GAGCGCACTT TTCGGCGGA
3841 GTGCAGAGCT CCCTGGAGCG CCAGTGTGCA CAGCGGGCAC GCCCCTTTGG CACGACTGGC
3901 TCGGATAGGA CGACCCATGT GACGTGTGGA ACATCATGTC GCCCCGTC   TTTCCCCGAT
3961 ATTACGGGGG TTAGCTTGGC TTAGCTTAATCG CCTTGCAGCA CATCCCCGTC GTTTACAAC  GTCGTGACTG
4021 GGAAAACCCT GGCGTTACCC AACTTAATCG CCTTGCAGCA CATCCCCTT  ACTCCCCTT  TCGCCAGCTG
4081 GCGTAATAGC GAAGAGGCCC GCACCGATCG CCCTTCCCAA CAGTTGCGCA GCCTGAATGG
4141 CGAATGGCGC CTGATGCGGT ATTTCTCT  TCAGCATCTG TGCGGTATTT CACACCGCAT
4201 ATGGTGCACT CTCAGTACAA TCTGCTCTGA TGCCGCATAG TTAAGCCAGC CCCGACACCC
```

```
4261 GCCAACACCC GCTGACGCGC CCTGACGGGC TTGTCTGCTC CCGGCATCCG CTTACAGACA
4321 AGCTGTGACC GTCTCCGGGA GCTGCATGTG TCAGAGGTTT TCACCGTCAT CACCGAAACG
4381 CGGAGACGA AAGGGCCTCG TGATACGCCT ATTTTATAG GTTAATGTCA TGATAATAAT
4441 GGTTTCTTAG ACGTCAGGTG GCACTTTTCG GGGAAATGTG CGCGGAACCC CTATTTGTTT
4501 ATTTTCTAA ATACATTCAA ATATGTATCC CAATAACCCT TTCCGTGTCG GATAAATGCT
4561 TCAATAATAT TGAAAAAGGA AGAGTATGAG GCTCATGAGA TATTCAACAT TTCCGTGTCG CCCTTATTCC
4621 CTTTTTGCG GCATTTTGCC TTCCTGTTT TGCTCACCCA GAAACGCTGG TGAAAGTAAA
4681 AGATGCTGAA GATCAGTTGG GTGCACGAGT GGGTTACATC GAACTGGATC TCAACAGCGG
4741 TAAGATCCTT GAGAGTTTTC GCCCCGAAGA ACGTTTTCCA ATGATGAGCA CTTTTAAAGT
4801 TCTGCTATGT GGCGCGGTAT TATCCCGTAT TGACGCCGGG CAAGAGCAAC TCGGTCGCCG
4861 CATACACTAT TCTCAGAATG ACTTGGTTGA GTACTCACCA GTCACAGAAA AGCATCTTAC
4921 GGATGGCATG ACAGTAAGAG AATTATGCAG TGCTGCCATA ACCATGAGTG ATAACACTGC
4981 GGCCAACTTA CTTCTGACAA CGATCGGAGG ACCGAAGGAG CTAACCGCTT TTTTGCACAA
5041 CATGGGGGAT CATGTAACTC GCCTTGATCG TTGGGAACCG GAGCTGAATG AAGCCATACC
5101 AAACGACGAG CGTGACACCA CGATGCCTGT AGCAATGGCA ACAACGTTGC GCAAACTATT
5161 AACTGGCGAA CTACTTACTC TAGCTTCCCG GCAACAATTA ATAGACTGGA TGGAGGCGGA
5221 TAAAGTTGCA GGACCACTTC TGCGCTCGGC CCTTCCGGCT GGCTGGTTTA TTGCTGATAA
5281 ATCTGGAGCC GGTGAGCGTG GGTCTCGCGG TATCATTGCA GCACTGGGGC CAGATGGTAA
5341 GCCCTCCCGT ATCGTAGTTA TCTACACGAC GGGGAGTCAG GCAACTATGG ATGAACGAAA
5401 TAGACAGATC GCTGAGATAG GTGCCTCACT GATTAAGCAT TGGTAACTGT CAGACCAAGT
5461 TTACTCATAT ATACTTTAGA TTGATTTAAA ACTTCATTTT TAATTTAAAA GGATCTAGGT
5521 GAAGATCCTT TTTGATAATC TCATGACCAA AATCCCTTAA CGTGAGTTTT CGTTCCACTG
5581 AGCGTCAGAC CCCGTAGAAA AGATCAAAGG ATCTTCTTGA GATCCTTTTT TTCTGCGCGT
5641 AATCTGCTGC TTGCAAACAA AAAAACCACC GCTACCAGCG GTGGTTTGTT TGCCGGATCA
5701 AGAGCTACCA ACTCTTTTTC CGAAGGTAAC TGGCTTCAGC AGAGCGCAGA TACCAAATAC
5761 TGTCCTTCTA GTGTAGCCGT AGTTAGGCCA CCACTTCAAG AACTCTGTAG CACCGCCTAC
5821 ATACCTCGCT CTGCTAATCC TGTTACCAGT GGCTGCTGCC AGTGGCGATA AGTCGTGTCT
5881 TACCGGGTTG GACTCAAGAC GATAGTTACC GGATAAGGCG CAGCGGTCGG GCTGAACGGG
5941 GGGTTCGTGC ACACAGCCCA GCTTGGAGCG AACGACCTAC ACCGAACTGA GATACCTACA
6001 GCGTGAGCTA TGAGAAAGCG CCACGCTTCC CGAAGGGAGA AAGGCGGACA GGTATCCGGT
6061 AAGCGGCAGG GTCGGAACAG GAGAGCGCAC GAGGGAGCTT CCAGGGGGAA ACGCCTGGTA
6121 TCTTTATAGT CCTGTCGGGT TTCGCCACCT CTGACTTGAG CGTCGATTTT TGTGATGCTC
6181 GTCAGGGGGG CGGAGCCTAT GGAAAAACGC CAGCAACGCG GCCTTTTTAC GGTTCCTGGC
6241 CTTTTGCTGG CCTTTTGCTC ACATGTTCTT TCCTGCGTTA TCCCCTGATT CTGTGGATAA
6301 CCGTATTACC GCCTTTGAGT GAGCTGATAC CGCTCGCCGC AGCCGAACGA CCGAGCGCAG
6361 CGAGTCAGTG AGCGAGGAAG CGGAAGA
```

```
2101 AAGGACACAA TGGGGTAACC ATACCAGCTC CAAAGAGGTC CAAGACGATG TTAATGATCT
2161 TCTCATCTGA CAGCTGGACA TTGGCGTTCT CATCCAGCTG CTTCTCCTGA CAGTGCTCAA
2221 TCAGGCTGTC TGTGATGTCC CGGATGTGGC CCTTAGGTAG GGAAAGTCCA CAGGTGAGCA
2281 AGATCTCAAA CCCAGAGCTA CCTCTCCATC CAGGTCTGGT CCTTCACTAT TCCTAGCACA
2341 TTTGTTCTGG AGGTGATGCC CCCTGAGGCT GTGTCCCAG CTCTCTCTG CCTCTGCAAG
2401 GCTCTCTCCT ACTACCTTAG AATGCTGCTA ATGGGACTC ATGGGACATT TGACACACAG
2461 CGTCTTGTAC TGTTATCATC TGGATGTGCT CTTTATCTTC TTTCTATTAT GAGGCCAGGA
2521 GATGAACTCT TTAACTCTTC CTGGCTCCCT CAGCAACTGC CCCAGGGTCC TGCATGTAAT
2581 GACTCTTCAG TGGCTATTGC TGTCTGTGGA AGCATGGAAG GGTTAGTCAA GATAAAGTTC
2641 TATTTCCCTG CCAAGGAAGA AGACTATTCC ACAACTGGCT TCAAGATCCC AGGTTGAAGC
2701 CTTCCTGAGA ACTTGCCAAG CCCCATGCAG TTCCTCTTAC CTTTGACCTC CCAGGCCCTG
2761 ATGCCATCTG CTTCCCACCA CCCACCTGCC TTTCCCCAGA CTGTACCTTC TCAAAGGTTT
2821 TGTAGTGCTC CTTGACCATC TTCTGCATGA AGCTGTAGAA CTTCTCATTC AGGTCCTTGA
2881 AGGCATTCAG GGAAGGGTTG GGTAGGTAGC GAAGAATAGG GATGAAGTCA GCTGGGTTTC
2941 CAGAGCCAAC CACCTCCCCG AAATTATTAT TCAGGTTGAC TAGGCTAAGC AGTTCTTGGT
3001 GGTTGTGGTC ATAGCGCCGG CCAAAGCAAA TGGCACAGAT GACATTGGTC ACTGATACCA
3061 CCACATACCT GTAGGGGTTA AGTGCCCAG GCCCTGCCAT CAGCTCCTGC AACGTGCTTA
3121 TCAGGACCTC AGCCTCCCTG CTCACATGCT CTTCCAGGTA GCAGGAGGTT GAGGAGGCTG
3181 GGTCAGAGGC AATGGAGAAA CTTTTCAGGC CATTCTGGGC CAGGCGCCGG CGGGCAGCCC
3241 ACACTGGTCC AGAGTCTGGG CTGAAGGACA TGCTCTGACC ATTACTGATG AGGGTGAAGG
3301 TGTAGAGGTC GGGCCGGACC CGCCCTGCCG CACCAGGGCC TGCCGGATGG
3361 TGTCCAGGCC GCTCAGCACC TGGAAATCAT CGCCCTGCCG TGGAGCCAAT TCGGATCTGC AGCACGTCCC
3421 CATACTGCTG GCTCATCCTT ACCACGGGTG GGTGCGGGTT CTTTCCCAGG GTCAGCATGT
3481 GCCCAATCAG AGGCCAGCCC GACAGTGCCA GGTGCCCCTG GTGGATTCTT CAGGCCTTTG GGGACCTGAG
3541 GTCTTGAGGC CCTGATTACC CAGAATACCA GTGCGGGGTT GACAGAAGAT AGAAGAAACT
3601 CCGTGGCCGA CATGGAGATT GGGAAAAGCA TGATCTGGTG AAGCTGGAGC TACGGAGTAA
3661 GTGAGAGAA GGTACTCAGG ACGTTGAAGT CGTGGTGACG CTTAGAGGAC AGCCTGCCCT
3721 CTTTATAGTC GTTGGACGAG TCCGGGCGCA AAGGTTTGC ACCCAGCAGG CGGTTGCTCC
3781 AGCCCACGCA TAGTCACGCG CCCGCGTCC TGCCAGAGCC GAGCGCACTT TTCGGCGGA
3841 GTGCAGAGCT CCCTGGAGCG CCAGTGTGCA CAGCGGGCAC GCCCCTTTGG CACGACTGGC
3901 TCGGATAGGA CGACCCATGT ACGTGTGGA ACATCATGTC CCTATAGTGC TTTCCCGAT
3961 ATTACGGGGG CGAGCTCGAA TTAGCTTGGC ACTGGCCGTC GTTTACAAC GTCGTGACTG
4021 GGAAACCCT GGCGTTACCC CCTTGCAGCA CATCCCCTT TCGCCAGCTG
4081 GCGTAATAGC GAAGAGGCCC GCACCGATCG CCCTTCCCAA CAGTTGCGCA GCCTGAATGG
4141 CGAATGGCGC CTGATGCGGT ATTTTCTCCT TACGCATCTG TGCGGTATTT CACACCGCAT
4201 ATGGTGCACT CTCAGTACAA TCTGCTCTGA TGCCGCATAG TTAAGCCAGC CCCGACACCC
```

```
4261 GCCAACACCC GCTGACGCGC CCTGACGGGC TTGTCTGCTC CCGGCATCCG CTTACAGACA
4321 AGCTGTGACC GTCTCCGGGA GCTGCATGTG TCAGAGGTTT TCACCGTCAT CACCGAAACG
4381 CGCGAGACGA AAGGGCCTCG TGATACGCCT ATTTTATAG GTTAATGTCA TGATAATAAT
4441 GGTTTCTTAG ACGTCAGGTG GCACTTTTCG CGCGGAACCC CAATAACCCT CTATTGTTT
4501 ATTTTCTAA ATACATTCAA ATATGTATCC GCTCATGAGA CAATAACCCT GATAAATGCT
4561 TCAATAATAT TGAAAAAGGA AGAGTATGAG TATTCAACAT TCCGTGTCG CCCTTATTCC
4621 CTTTTTTGCG GCATTTTGCC TTCCTGTTTT TGCTCACCCA GAAACGCTGG TGAAAGTAAA
4681 AGATGCTGAA GATCAGTTGG GTGCACGAGT GGGTTACATC GAACTGGATC TCAACAGCGG
4741 TAAGATCCTT GAGAGTTTTC GCCCCGAAGA ACGTTTTCCA ATGATGAGCA CTTTAAAGT
4801 TCTGCTATGT GGCGCGGTAT TATCCCGTAT TGACGCCGGG CAAGAGCAAC TCGGTCGCCG
4861 CATACACTAT TCTCAGAATG ACTTGGTTGA GTACTCACCA GTCACAGAAA AGCATCTTAC
4921 GGATGGCATG ACAGTAAGAG AATTATGCAG TGCTGCCATA ACCATGAGTG ATAACACTGC
4981 GGCCAACTTA CTTCTGACAA CGATCGGAGG ACCGAAGGAG CTAACCGCTT TTTGCACAA
5041 CATGGGGAT CATGTAACTC GCCTTGATCG TTGGGAACCG GAGCTGAATG AAGCCATACC
5101 AAACGACGAG CGTGACACCA CGATGCCTGT AGCAATGGCA ACAACGTTGC GCAAACTATT
5161 AACTGGCGAA CTACTTACTC TAGCTTCCCG GCAACAATTA ATAGACTGGA TGGAGGCGGA
5221 TAAAGTTGCA GGACCACTTC TGCGCTCGGC CCTTCCGGCT GGCTGGTTTA TTGCTGATAA
5281 ATCTGGAGCC GGTGAGCGTG GGTCTCGCGG TATCATTGCA GCACTGGGGC CAGATGGTAA
5341 GCCCTCCCGT ATCGTAGTTA TCTACACGAC GGGGAGTCAG GCAACTATGG ATGAACGAAA
5401 TAGACAGATC GCTGAGATAG GTGCCTCACT GATTAAGCAT TGTAACTGT CAGACCAAGT
5461 TTACTCATAT ATACTTTAGA TTGATTTAAA ACTTCATTTT TAATTTAAAA GGATCTAGGT
5521 GAAGATCCTT TTTGATAATC TCATGACCAA AATCCCTTAA CGTGAGTTTT CGTTCCACTG
5581 AGCGTCAGAC CCCGTAGAAA AGATCAAAGG ATCTTCTTGA GATCCTTTTT TTCTGCGCGT
5641 AATCTGCTGC TTGCAAACAA AAAAACCACC GCTACCAGCG GTGGTTTGTT TGCCGGATCA
5701 AGAGCTACCA ACTCTTTTTC CGAAGGTAAC TGGCTTCAGC AGAGCGCAGA TACCAAATAC
5761 TGTCCTTCTA GTGTAGCCGT AGTTAGGCCA CCACTTCAAG AACTCTGTAG CACCGCCTAC
5821 ATACCTCGCT CTGCTAATCC TGTTACCAGT GGCTGCTGCC AGTGGCGATA AGTCGTGTCT
5881 TACCGGGTTG GACTCAAGAC GATAGTTACC GGATAAGGCG CAGCGGTCGG GCTGAACGGG
5941 GGGTTCGTGC ACACAGCCCA GCTTGGAGCG AACGACCTAC AGCGTGAGCTA GATACCTACA
6001 GCGTGAGCTA TGAGAAAGCG CCACGCTTCC CGAAGGGAGA AAGGCGGACA GGTATCCGGT
6061 AAGCGGCAGG GTCGGAACAG GAGAGCGCAC CGAGGGAGCTT CCAGGGGGAA ACGCCTGGTA
6121 TCTTTATAGT CCTGTCGGGT TTCGCCACCT CTGACTTGAG CGTCGATTTT TGTGATGCTC
6181 GTCAGGGGGG CGGAGCCTAT GGAAAAACGC CAGCAACGCG GCCTTTTTAC GGTTCCTGGC
6241 CTTTTGCTGG CCTTTTGCTC ACATGTTCTT TCCTGCGTTA TCCCCTGATT CTGTGGATAA
6301 CCGTATTACC GCCTTTGAGT GAGCTGATAC CGCTCGCCGC AGCCGAACGA CCGAGCGCAG
6361 CGAGTCAGTG AGCGAGGAAG CGGAAGA
```

METHOD AND CELL LINE FOR TESTING MUTAGENICITY OF A CHEMICAL

TECHNICAL FIELD

The present invention relates to in vitro test systems used for assessing cytotoxicity and genotoxicity of chemicals. More specifically, the present invention relates to in vitro test systems which replace whole animal models currently used for such tests and is particularly useful for testing the cytotoxicity and genotoxicity of chemicals, the toxicity of the chemicals requiring metabolic activation.

BACKGROUND ART

It is desirable to develop non-animal models for assessing cytotoxicity and genotoxicity of chemicals in humans. Accordingly, a human cell culture system offers the advantage of species identity and eliminates the need to extrapolate results from experiments in rodent or bacterial cells.

Metabolic activation is essential for the conversion of a wide variety of chemicals to ultimate cytotoxic or genotoxic agents. It is therefore desirable to provide a toxicological test system which is proficient in bioactivation of xenobiotics in order to reveal the toxicologic potential of an agent. Cytochromes P450 comprise the most important class of enzymes that bioactivate xenobiotics.

Cytochromes P450 are implicated in the activation of many cytotoxic agents, pro-mutagens and cancer chemotherapy agents. In particular, cytochrome P450IAI (CYP1A1) has been implicated in lung cancer by virtue of its ability to bioactivate components of cigarette smoke such as benzo(a)pyrene into potent mutagenic agents.

The prokaryotic test system most commonly used to detect mutagenicity at the present time is the Ames test (1). The Ames test is limited by the fact that bacteria used in the test lack bioactivating enzymes such as the cytochromes P450. Therefore the system cannot detect the mutagenicity of agents requiring metabolic activation.

A modified Ames test (2) has been developed which includes premetabolism by microsomal preparations. This test suffers from the fact that many agents, once metabolized to their active forms, are unable to cross the plasma membrane to enter the cells. In other words, the extracellular location of the enzymes greatly prejudices the effectiveness of the test. It is therefore further desirable to provide a test system consisting of mammalian cells metabolically competent for bioactivation.

There have been many approaches used by researchers to develop cell lines for use as test systems for bioactivation of chemicals. Each of these approaches are deficient in at least one aspect if not many aspects. With regard to these type of tests, there are three important considerations for developing engineered mammalian cell lines for examining bioactivation of chemicals and assessing their toxologic potential.

The first consideration is appropriate and stable expression of the chimeric gene construct. For example, Chinese hamster ovary cells have been transformed with rat cytochrome P450 IA1 (CYP1A1,(3)) and IIB1 (CYP2B1,(4)) cDNAs in an expression vector. The expression of the P450 CDNA in the vector is controlled by the strong, constitutive SV40 early promotor. One cell line had a few copies of the CYP1A1 but the other two had many copies. One of the high copy transformants produced several bands on genomic Southern blot strongly hybridizing with CYP1A1 probe suggesting rearrangement of the integrated genes. Multi-copy integration events are often unstable and the multi-copy CYP1A1 transgenes in these CHO lines are no exception (3). One of the lines is losing copies and the very high copy number transformant appears to be amplifying the transgene. Only one of the three is reported to be relatively stable. Only the relatively stable transformant and the low copy transformant show increased mutagenicity upon exposure to benzo(a)pyrene (BAP) and BAP-(trans)-7,8-diol, two compounds which are mutagenic only after metabolism by CYP1A1.

These studies show that expression of CYP1A1 or CYP2B1 resulted in an increased mutagenicity after exposure of the cells to compounds known to be bioactivated by these enzymes. However, the number of transformants obtained which remain stable in their expression of the P450 transgenes is few. It is hypothesized that this is due to the promotor used in the expression vector being a strong constitutive promotor in most situations. Constant, high levels of P450 expression can be deleterious to the cells. It is more desirable to have a P450 cDNA under control of an inducible promotor of moderate strength as opposed to the strong constitutive promotor used in the prior art.

The second consideration is the ability to draw conclusions about dose level in the human situation. One aspect of the problem is that human cells are more complete in their capability for DNA repair than are rodent cells which concentrate their repair efforts on transcriptionally active regions of the chromatin. Transformation of human cells with P450 cDNAs in expression vectors is more desirable for drawing conclusions about mutagenic doses in humans.

Other researchers have initiated studies of transfected cytochrome P450 cDNAs in human lymphoblasts (4,5,6). This system addresses the species specificity problem but does not allow for inducible expression of P450 as does the vector used to transform human cells in accordance with the present invention.

Very recent research has been directed to applying a mutant hamster cell line deficient in DNA repair to problems in environmental mutagenesis by introducing the mouse cytochrome $P_3450$ (P4501A2 subfamily) gene for metabolic activation of aromatic amines (6a). Others suggest an in vitro mutagenic system based on activation by human P450s to supplement other test systems (6b).

A third consideration is the ability to assess gene specific DNA damage. Comparison of DNA damage in specific genes is facilitated by using cells which do not repair any of the damage sites. For this reason, it is desirable to use human DNA excision repair deficient cells in addition to normal DNA repair proficient cells.

SUMMARY OF THE INVENTION

In accordance with the present invention, there is provided a method of testing for mutagenicity of a chemical by exposing test cells to the chemical in vitro, intracellularly metabolizing the chemical into a mutagenic metabolite, and detecting gene damage in the test cells as an indication of mutagenicity of the chemical.

The present invention further provides a cell line, for testing mutagenicity by a chemical consisting essentially of fibroblasts which normally have no detectable cytochrome P450 mixed function oxidase enzyme activity, the fibroblasts being transformed with chimeric gene constructs containing cytochrome P450 coding sequences and having intracellular cytochrome P450 oxidative metabolizing activity.

BRIEF DESCRIPTION OF THE DRAWINGS

Other advantages of the present invention will be readily appreciated as the same becomes better understood by reference to the following detailed description when considered in connection with the accompanying drawings wherein:

FIG. 3a is the DNA sequence of construct pRNH127;

FIG. 3b is the DNA sequence of pRNH155;

DETAILED DESCRIPTION OF THE INVENTION

Figure 1:
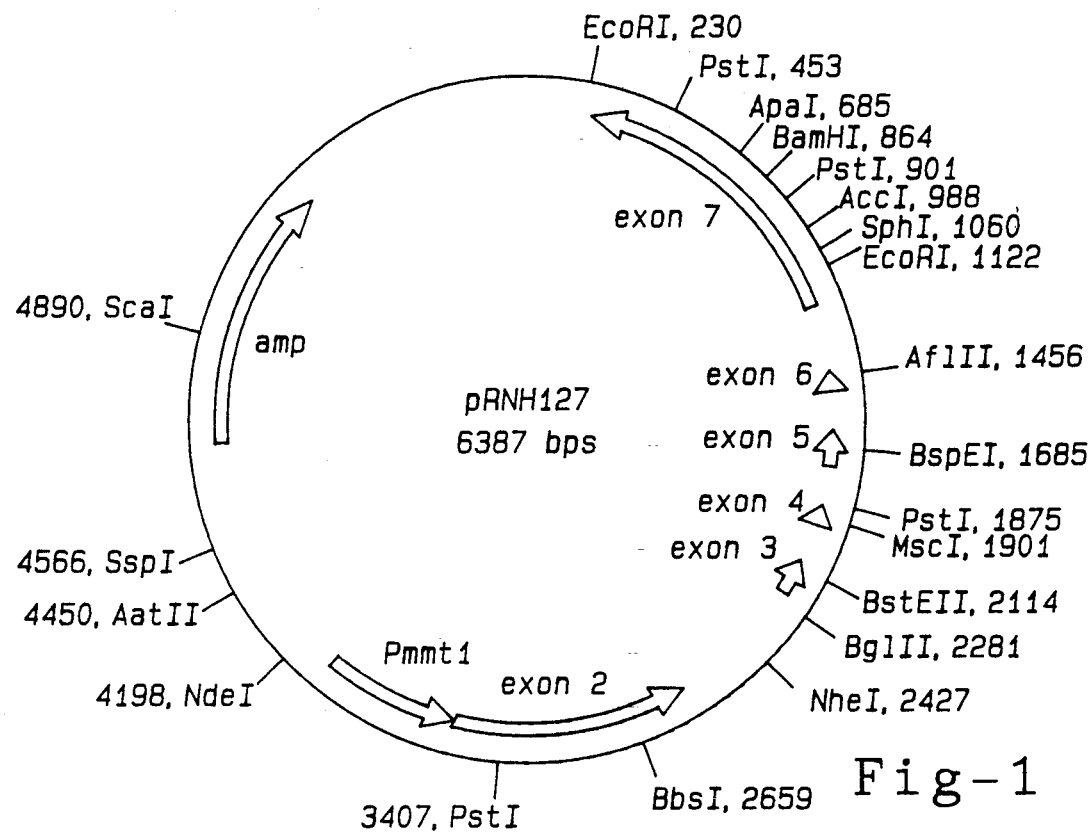
FIG. 1 is a map of the pRNH127 construct.

The present invention provides a method of testing for mutagenicity of a chemical, the method generally including the steps of exposing test cells to the chemical in vitro, intracellularly metabolizing the chemical into a mutagenic metabolite, and detecting gene damage in the test cells as an indication of mutagenicity of the chemical. The invention differs from existing technology by the engineering of cells such as human fibroblasts with an inducible chimeric gene for expressing enzymes which metabolize chemicals. Unlike prior art technologies, such as the Ames test, the present invention tests for mutagenicity by utilizing human cells containing chemical metabolizing enzymes whereas the most commonly used test used prokaryotic cells which need to be supplemented extracellularly with the enzymes active in the metabolism of the chemicals. Moreover, the eukaryotic prior art systems include cells containing protective enzymes which can detoxify the metabolized chemicals thereby resulting in a false negative mutagenicity test. Hence, the present test method provides a balance between metabolic activation, detoxification and toxicity/mutagenicity which approximates those inherent in normal human cells.

The preferred test cell used in accordance with the present invention are cells which normally have no detectable cytochrome P450 mixed function oxidase enzyme activity. Examples of such cells are human skin fibroblasts derived from xeroderma pigmentosum group A (XPA) and DNA repair normal donors, and human epithelial cells. The human fibroblast cells are preferred because fibroblasts are adherent and readily form colonies which are easy to count in a test system. Unlike prior art systems which use human lymphoid cells which are nonadherent to a test plate and therefore cause difficulties in counting surviving colonies in a test system, the present invention preferably utilizes fibroblasts which are adherent to a test plate and form colonies which are easily counted. More specifically, a common system for detection of mutagenicity includes a plating step wherein cells are grown on plates in media in a dose response test to a chemical. Surviving cells are counted in media which is selective for the mutant thereby indicating the relative mutagenicity of a chemical in a dose response test. (Dose response test meaning different plates containing cells are exposed to increasing concentrations of the chemical). Increased cell survival of the mutated cells which are the only cells that survive in the test media are an indication of response to chemical, this being shown in a dose dependent manner.

As stated above, test cells are used, which, in their normal state, do not include intracellular cytochrome P450 mixed function oxidase enzymes. The test cells are transformed to express the chemical metabolizing enzymes, preferably including an inducible promotor. That is, the test cells are preferably fibroblasts normally not including any cytochrome P450 oxidative activity. The test cells are transformed to express cytochrome P450 enzymes such that the metabolizing step discussed above is more specifically defined as oxidatively metabolizing the chemical within the fibroblasts through the intracellular cytochrome P450 mixed function oxidase enzyme expressed by the transformed fibroblasts.

Figure 2:
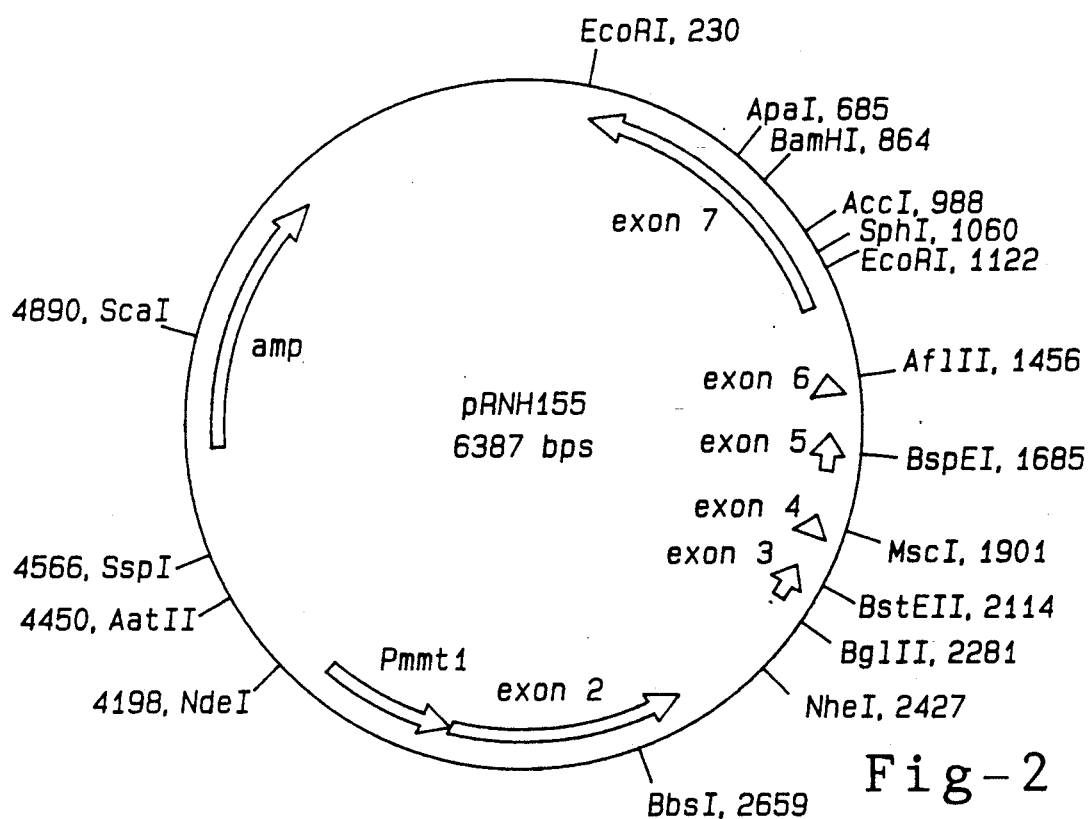
FIG. 2 is a map of the pRNH155 construct.
Figure 3D:
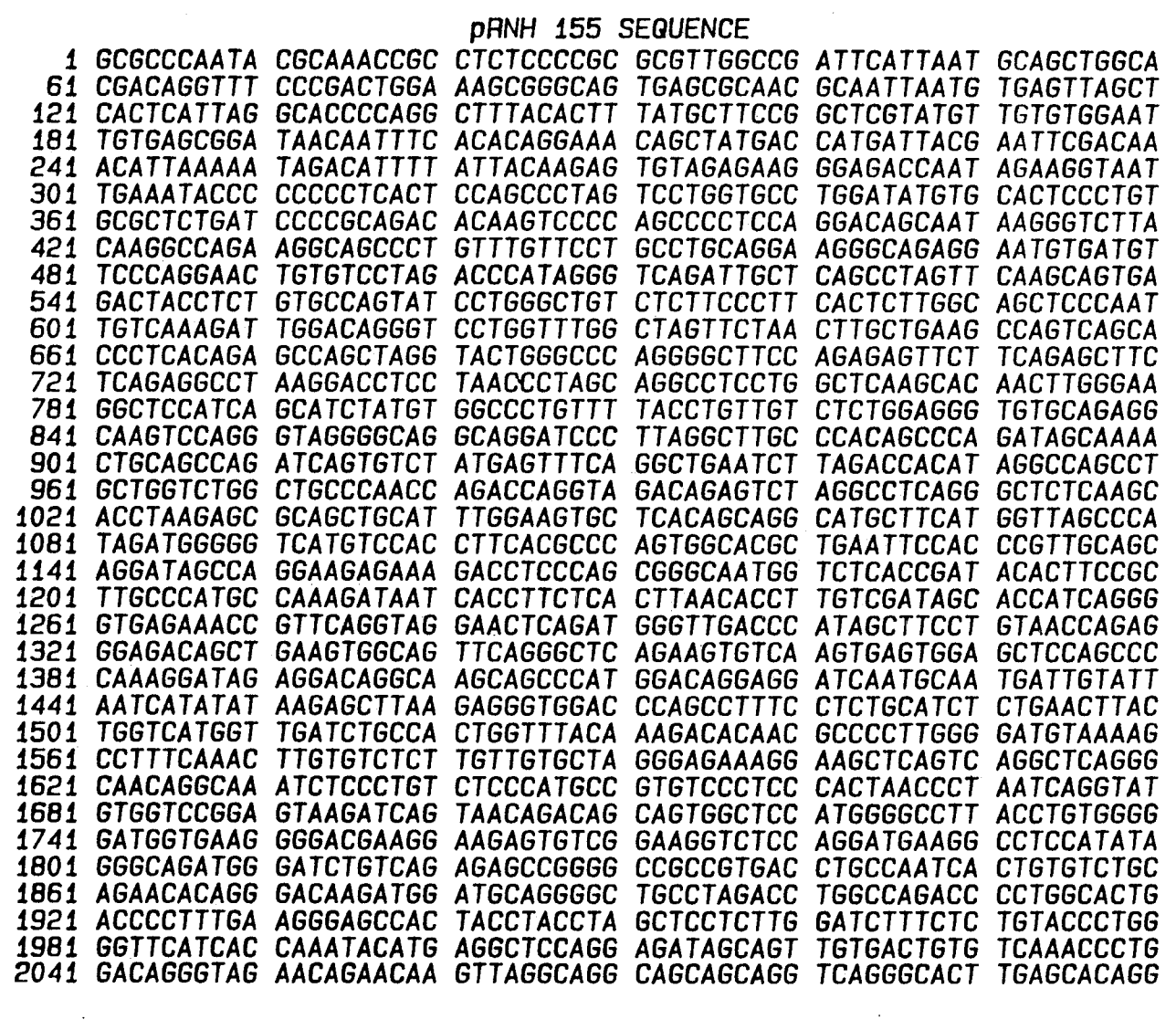

Preferably, the human XPA fibroblasts are transformed by the introduction of a chimeric cytochrome P450IA1 (CYP1A1) expression construct. FIGS. 1 and 2 show maps of the pRNH127 construct, a 6387 bp construct, and the pRNH155 construct, respectively, the latter a 6387 bp construct. FIGS. 3a and b show the base sequence for the pRNH127 and pRNH155 constructs, respectively.

The pRNH127 construct is a mouse metallothionein (MMT-1) CYP1A1 expression vector that was constructed by first isolating the MMT-1 promotor from p13MMT as an EcoRI/HinDIII fragment, and trimming the ends with HaeIII and Sau3AI. This fragment was force cloned into pRNH62 that had been digested with HinDIII, treated with T4 DNA polymerase to prepare blunt-ends and then digested with BclI (thereby eliminating intron 1 sequences).

pRNH155 is the same clone that was constructed using a different strategy. A MMT-1 CYP1A1 expression vector was constructed by first isolating the MMT-1 promotor from p13MMT as a 467 base pair Sau3AI fragment which was then cloned into pRNH1 that had been digested with BclI. After verifying the correct orientation of the promotor with EcoRI, CYP-1A1 intron 1 sequences were removed by digesting to completion with HinDIII, followed by a partial EcoRI digest. The 5491 bp band representing the desired deletion was isolated, treated with T4 DNA polymerase to repair the ends, and then ligated to close the plasmid. The 3' end of the CYP1A1 gene was isolated from pRNH59 as an 895 bp EcoRI fragment and then cloned into the now unique EcoRI site of the intermediate plasmid. Orientation was verified by digestion by BamHI/BglII.

Figure 4:
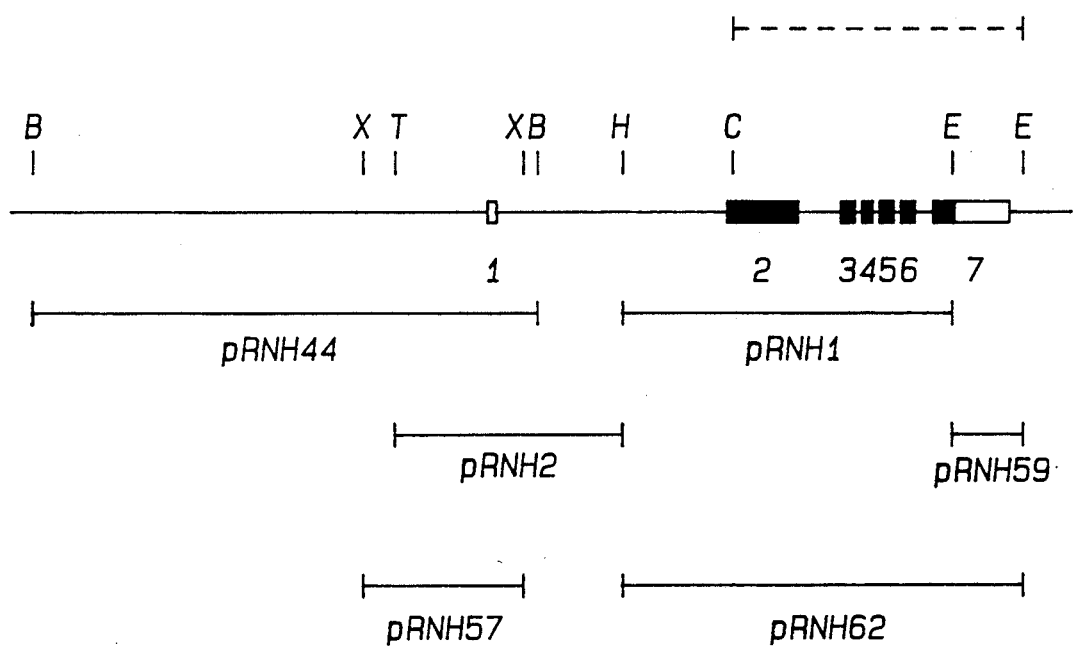
FIG. 4 is a partial map of the 5830 bp human CYP-1A1 gene.

FIG. 4 shows a partial map of the 5830 base pair human CYP1A1 gene. In the Figure, the open boxes represent non-coding exon information and the closed boxes represent coding exon information. The position of restriction endonuclease recognition sites are shown for BglII(B), BclI(C), EcoRI(E), HinDIII(H), TaqI(T), and XbaI(X). The information contained in the various subclones is shown below the map. The BclI/EcoRI fragment containing CYP1A1 coding information cloned into expression vectors to be used is denoted by the broken line.

The present invention preferably uses fibroblasts transformed to express the cytochrome P4501A1 mixed function oxidase enzyme. The cytochrome P450 mixed function oxidase enzyme family catalyzes the oxidative metabolism of a variety of xenobiotics in mammalian cells including environmental protoxicants, steroid hormones, cancer chemotherapeutic agents, and procarcinogens. As a result of cytochrome P450-mediated metabolism, certain compounds are converted to reactive intermediates which are capable of damaging cellular macromolecules. The mammalian cytochrome P450 gene superfamily includes at least eight gene families (7-9). Experiments on rat and liver have demonstrated that some of the cytochrome P450 gene families produce at least 20 separate cytochrome P450 enzyme forms. The tissue specificity of cytotoxicity and carcinogenesis caused by some xenobiotics may be related to the tissue specific expression of cytochromes P450 which activate those compounds.

Because of this relationship of the cytochrome P450 to chemical activation of procarcinogens to carcinogens, applicant chose the P450 system to be incorporated into the test cells. Applicant specifically chose the CYP1A1 activity as this gene is well characterized. In particular, cytochrome P4501A1 has been implicated in lung cancer by virtue of its ability to bioactivate components of cigarette smoke such as benzo(a)pyrene into potent mutagenic/carcinogenic agents.

As discussed above, the construct used preferably in accordance with the present invention includes the mouse metallothionein promoter (MMT-1). Unlike prior art systems which utilize the strong constitutive SV40 early promotor, the present invention preferably uses an inducible promotor of moderate strength. Preferably, the MMT-1 promotor is easily induced by exposure of cells to nontoxic levels of metals such as zinc or cadmium. Accordingly, control cells can be made directly in accordance with the present invention but are not exposed to the inducible levels of metals whereas test cells are exposed to metals such as zinc or cadmium to induce expression of the CYP1A1 activity. Since the MMT-1 promotor only requires nontoxic levels of the metals, this being previously well characterized (9a) the test cells include an internal control mechanism which has no effect on the cells which would alter test results.

A further advantage of using fibroblast cells such as the XPA cells is the fact that the XPA cells are produced from a human autosomal recessive genetic disorder caused by the inability to repair DNA damage caused by ultraviolet light and chemicals which form bulky DNA adducts (10-12). XPA cells are capable of repairing other types of DNA damage such as single strand breaks caused by ionizing radiation (13). The genetics of xeroderma pigmentosum (XP) have been defined unusually well by somatic cell fusion studies using fibroblast lines established from approximately 100 individuals with XP disorder. Members of XP complementation group A (XPA) exhibit the lowest DNA excision repair capacity (14) and therefore are most sensitive to DNA damage. Thus, these cells provide the most sensitivity for detection of agents which exert cytotoxic and genotoxic effects by bulky adduct damage to DNA.

Various methods have been used for the detection of gene damage in test cells as an indication of mutagenicity of a chemical. For example, gene specific DNA damage resulting from UV exposure has been monitored by an elaborate method making use of bacterial or bacteriophage pyrimidine dimer specific endonucleases and Southern blotting of DNA treated with these endonucleases and separated in denaturing gels (15). An analogous procedure using the E. coli ABC-excision nuclease has been useful in analyzing large adduct DNA damage (16). Other methods to measure large adduct DNA damage have recently been developed (17). This latest method exploits the inability of Taq DNA polymerase to utilize DNA containing large adduct damage as a template for DNA synthesis. A consequence of this phenomenon is that polymerase chain reaction (PCR) amplification of a region containing such damage is reduced proportionately to the number of damaged segments in the sample. One can use the decrease in PCR amplification to measure the amount of damage sustained by a specific DNA segment in a population of cells. Additionally, by performing the assay at various time points after exposure to a damaging agent, the rate of repair of a specific segment can also be monitored and compared to the rate of repair of other segments. This is a powerful assay which can be performed relatively quickly and easily.

Preferably the present invention utilizes oligonucleotides flanking the mutational hot spots in the p53 gene as primers for PCR assay of gene specific DNA damage. These oligonucleotides have been used by others to amplify these regions of the p53 gene (18). This method produces fragments of appropriate size for the DNA damage assay detailed below. Similarly, oligonucleotides for the ras gene are used to monitor DNA damage in that gene as discussed below.

More specifically, the following assays are used to test for gene specific DNA damage, mutagenicity, and cytoxicity.

a. Gene specific DNA damage assay

This assay is adapted from Govan et al, Nucleic Acids Research 18:3823-3830 (1990):

Quantitative polymerase chain reaction (PCR) amplification is performed by limiting the amount of template DNA such that the yield of product is linearly proportional to input DNA levels. This normally is achieved in the range of 10 to 200 ng input genomic DNA. In order to quantitate the product, 0.1 $\mu$Ci $\alpha$-$^{32}$P-dCTP is added to the reaction such that the product will be radiolabelled. PCR products are fractionated by gel electrophoresis and visualized by staining in 0.1 $\mu$M ethidium bromide. The gel is dried and autoradiographed by exposing it to X-ray film. The autoradiogram is used to localize the labelled product which is then excised and the incorporated $^{32}$P is measured by scintillation spectrometry. This serves as a measure of product formation.

b. Mutagenicity assay:

Mutations in the hypoxanthine-phosphoribosyltransferase (HPRT) gene induced by exposure of cells to chemicals are quantified in a dose-response experiment and used as a measure of mutagenicity. The HPRT gene is on the X chromosome and therefore, only one copy is active in mammalian cells. This provides an appropriate single copy gene for mutation studies.

The assay is performed on cells that are induced for expression of CYP1A1 and on control uninduced cells. After incubation plus (induced) and minus (uninduced) metal ions, the cells are exposed to various doses of chemical (i.e. 1 to 50 $\mu$M benzo(a)pyrene) for a set time period. After exposure to chemical, the cells are washed and harvested and then replated at lower density in media containing 6-thioguanine (7 $\mu$g/ml) to select for cells with mutated HPRT gene. Colonies which form from the growth of single cells with mutated HPRT genes are counted. The colony numbers serve as the data points. If a chemical, such as benzo(a)pyrene, is metabolized to a mutagenic compound by CYP1A1, many more colonies will result at any given does from the cells induced for expression of CYP1A1.

c. Cytotoxicity assay:

The cytotoxicity assay is similar to the mutagenicity assay except that non-selective media is used. Cells induced or uninduced for CYP1A1 expression and exposed to various doses of chemical are washed, harvested and replated at lower density in normal media and allowed to form colonies. Cytotoxicity is indicated by a decrease in the number of colonies with increasing dose of chemical. Metabolic activation of chemical by CYP1A1 is indicated by a further decrease in number of colonies formed at a given dose by cells induced for CYP1A1 expression.

EXPERIMENTATION

The following experiments provide the basis for using human cell lines developed as a suitable nonanimal substitute for the determination of the cytoxicity, genotoxicity, and potential carcinogenicity of a variety of compounds.

MATERIALS AND METHODS a Preparation of the CYP1A1 Expression Construct

CYP1A1 coding and polyadenylation sequences contained in plasmid pRNH62 (a genomic subclone, FIG. 4) was isolated and cloned into pUC8 (a cloning vector with a multiple cloning site) using standard recombinant DNA techniques. The mouse metallothionein-I (MMT-I) promoter fragment (containing one metal responsive element) was inserted into the pUC8-CYP1A1 clone in the proper orientation to direct the transcription of CYP1A1 sequences. This construct is co-transfected with a dominant selectable marker (pRSV-NEO) into both SV40 transformed XPA fibroblasts (GM4429 & GM4312) and DNA repair proficient SV40 transformed human fibroblasts (GM0637).

Single colonies of transfected cells are selected by incubation in media containing G-418. These colonies are then analyzed for constitutive and inducible expression of CYP1A1. The MMT-I promoter more appropriately approximates the expression levels of P450s in non-hepatic tissues. Other human P450 cDNAs obtained by RT-PCR from human liver mRNA (or PCR of human liver cDNA library DNA) can be inserted into the expression vector for transfection of human cells.

b. Transfections and Selection of Transformants

The XPA and normal fibroblasts have been obtained from the Genetic Mutant Cell Respository, Camden, N.J. The cell lines are SV40 transformed which is essential for them to be transfected efficiently and to be propagated eternally after transformation. The cell lines used are: XPA, GM4429 and GM4312; normal, GM0637. These cell lines are well characterized as to their DNA repair capabilities having been used by many laboratories over the years. The XPA and normal fibroblasts are transfected with Ca-PO$_4$ co-precipitates (19) of the CYP1A1 expression construct and pRSV-NEO (the NEO cartridge under control of the Rous sarcoma virus long terminal repeat). Several ratios (1:1, 5:1 & 10:1) of CYP1A1:pRSV-NEO DNA are used to increase the likelihood of obtaining transformants with a single copy, functional CYP1A1 chimeric gene construct. Transformants are selected by incubation in medium containing Geneticin (300 $\mu$g/ml).

Single colonies are isolated with cloning rings and propagated individually in media containing Geneticin at 75 $\mu$g/ml to assure maintenance of the transgenes. Only one colony is picked from a single plate to ensure that duplicate clones will not be picked. The inducibility of CYP1A1 is assayed in 24 well dishes with ethoxy-fluorescein ethyl ester (EFEE) as substrate (21). This assay can be performed on intact cells without cytotoxicity by overlaying the cell monolayer with phosphate buffered saline (PBS) containing EFEE. The cells are incubated for two hours and the PBS containing the EFEE and its metabolites is decanted, acidified and analyzed by thin layer chromatography. EFEE and fluorescein ethyl ester (FEE), the product of CYP1A1 metabolism of EFEE are easily separated and visualized under long wave UV illumination. Thus, CYP1A1 activity in induced and uninduced cells can be compared early after isolation of the clones before substantial propagation has occurred. Uninduced cells produce little or no FEE and induced cells produce ample amounts of FEE. Applicants have synthesized sufficient quantities to perform several thousand assays, verified the quality of the product by testing in HepG2 cells (FIG. 5) and used it to screen a small set of transformants (FIG. 6) with positive results as discussed below.

The copy number of both NEO and CYP1A1 constructs integrated is determined in genomic DNA from each individually propagated colony which shows inducible CYP1A1 activity. It is expected to obtain several colonies which fit the criteria of a single inducible copy of CYP1A1. This will provide several lines in which to test the xenobiotic activities. Thus, there is control for the potential variability which may be due to integration position of the transgenes.

Characterization of Transformants

The transformants are characterized with regard to: 1) copy number of CYP1A1 gene constructs, 2) expression levels of CYP1A1 mRNA in the uninduced state and induced by incubation with heavy metals, and 3) the levels of CYP1A1 protein and enzymatic activity in the uninduced state and induced by incubation with heavy metals which regulate the MMT-I promoter in the expression construct.

The copy number of CYP1A1 expression constructs present in the transgenes of individual transformants is assessed using quantitative PCR or slot blot analyses. Quantitative PCR has been used to quantitate bulky adduct DNA damage (17) and can be adapted easily to quantitate the copy number of integrated sequences. Oligonucleotide primers which specifically direct the amplification of the expression construct are used to amplify integrated sequences from genomic DNA of transformants. One oligonucleotide is derived from the MMT-I promoter sequences and the other derived from within the CYP1A1 coding sequences. Standardization is achieved by amplification of a single copy sequence such as the p53 gene to be analyzed for DNA damage (see below) and by reconstruction using non-transformant genomic DNA samples with CYP1A1 expression construct plasmid DNA added to simulate different copy numbers. Alternatively, slot blot or genomic Southern blot analyses can be used to quantitate the copy number of chimeric gene constructs in each transformant.

Expression of CYP1A1 mRNA is assessed by quantitative RT-PCR (PCR amplification of first strand cDNA prepared from mRNA of transformants) and confirmed by northern blot analyses using CYP1A1 cDNA as hybridization probe in specific instances (transformants to be used for further work). Oligonucleotides from two different exons within the CYP1A1 mRNA are used specifically to direct the amplification of mature mRNA sequences without interference from unexpressed native genes. CYP1A1 mRNA levels are assessed in dose response experiments wherein the expression of the CYP1A1 construct is induced by addition to the media of $CdSO_4$ from 1 to 10 $\mu M$. This is the range over which XPA cells transfected with a MMT-I promoted chloramphenicol acetyl transferase (CAT) gene displayed induction. Measurement of actin mRNA levels serve as internal controls for normalization in both RT-PCR and northern blot analyses.

CYP1A1 enzyme activity is quantitated using the ethoxyresorufin O-deethylase assay, essentially as described by Klotz et al. (22). The specificity of this reaction for the CYP1A1 isozyme has been well established in both animal models (23,24) and human tissue samples (24, 25). In brief, the reaction is carried out in 0.1M $KP_i$, pH7.8 containing 0.1M NaCl, 2 $\mu M$ ethoxyresorufin, 5 to 150 $\mu g$ of microsomal protein and 0.5 mM NADPH. The formation of resorufin is monitored at ($\epsilon 572 = 73$ $mM^{-1}cm^{-1}$). Alternatively, the same assay can be carried out using whole cell homogenate, but with the addition of 50 $\mu M$ dicumarol to inhibit the reduction of resorufin by cytosolic quinone oxidoreductase (26). Levels of CYP1A1 protein can also be monitored by Western blot using the antibody to rat CYP1A1. The time course of induction also will be monitored to determine the minimum exposure times necessary to achieve induction. In addition the decay of CYP1A1 activity after inducing agents are removed will be determined in order to define the maximum time during which xenobiotics may be metabolized.

d. Dose Response to Xenobiotics

Cells are seeded at $10^5$ cells per 6 cm dish and half the dishes are incubated in media containing 5 $\mu M$ $CdSO_4$ to induce the expression of the CYP1A1 construct. $CdSO_4$ is removed by washing the cells with phosphate buffered saline containing 5 mM EDTA after a suitable induction period. Xenobiotics are added to the media of both induced and uninduced cells. Initially, procarcinogens are applied in concentrations ranging from 1 to 50 $\mu M$ (19,20,67). In addition, the time course of exposure determined by using pulses of selected duration, starting with 1 hour. The time course data provide insight as to how quickly cytotoxic and genotoxic effects occur. After the pulse with procarcinogen, the cells are washed, harvested with trypsin and replated at lower density to allow for the formation of colonies. One set is incubated in the presence of 6-thioguanine to assay for mutation of the HPRT gene and one set is incubated in normal media to determine the cytotoxicity of the treatment.

RESULTS a Characterization of XPA Cells

In addition to using the XPA cells for transient expression of normal and mutant human adenosine deaminase cDNAs (27), the XPA cells have been used as a tool for the isolation of a normal human cDNA for the DNA repair gene defective in XPA cells. The approach used consists of complementing XPA cells by co-transformation with a dominant selectable marker gene and a normal human cDNA expression library (28). Using PCR, stably integrated cDNAs from the genomic DNAs of complemented XPA cells have been isolated in an effort to identify the complementing sequences. Data obtained from these studies indicate that, like other human cells, the XPA cells to be used with the present invention integrate few copies of a tranfected DNA and are unlikely to give high copy transformants. This is most useful for the production of a stable P450 chimeric gene copy number and a consistent expression level. Although the XPA cells integrate only a few copies of transfected DNAs (unpublished data), they do transform at high efficiency (19,28). As a result, transfection of these cells provides a large number of transformants which can be analyzed for copy number and expression.

b. Endogenous Levels of Cytochromes P450

Most cultured cells do not express P450 after long term culture (3,29). However, it was vital to establish that the cells used indeed do not express P450, in particular CYP1A1. Therefore, the levels of CYP1A1 and cytochrome P450 IIEI (CYP2E1) in GM4429 (XPA) and GM0637 (normal) fibroblasts were investigated by Western blot analyses using antibodies to the rat forms of these enzymes. No proteins corresponding to human CYP1A1 or CYP2E1 were detected by the antibodies. CYP1A1 is not normally present without induction. To ensure that the antibody to rat CYP1A1 would detect human CYP1A1, both XPA fibroblasts (GM4429) and HEPG2 cells (a human hepatoma cell line which expresses CYP1A1 when induced) were examined for the inducibility of CYP1A1 gene expression by a potent inducing agent, 2,3,7,8-tetrachlorodibenzofuran (TCDF) (FIG. 5).

Figure 5:
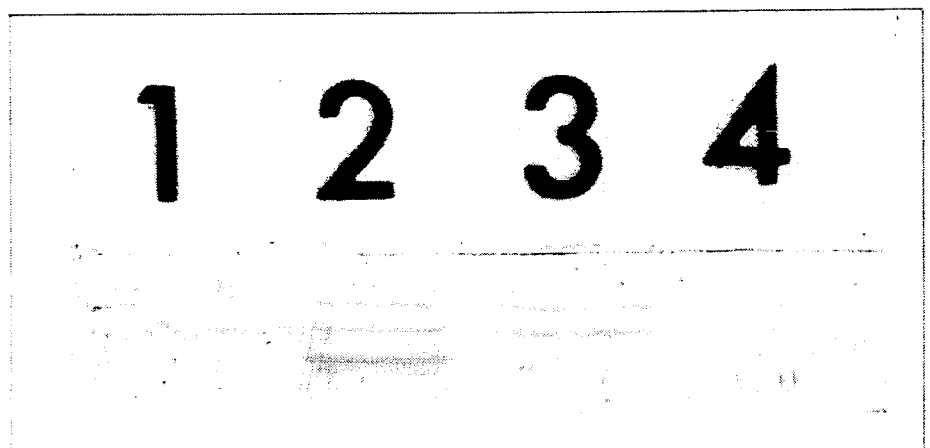
FIG. 5 shows induction of CYP1A1 detected by Western blot in HEPG2 cells but not in XPA fibroblasts.

FIG. 5 shows induction of CYP1A1 detected by western blot in HEPG2 cells but not in XPA fibroblasts. Cells were grown until approximately 75% confluent, then treated with 0.1 $\mu M$ 2,3,7,8-tetrachlorodibenzofuran (TCDF) or vehicle alone (ethanol). After 16 hours, the cells were harvested and microsomes were prepared. Microsomal proteins (10 $\mu g$) from each cell line were fractionated by SDS-PAGE, transferred to nitrocellulose membrane and probed with antibody to rat CYP1A1. The CYP1A1 induced by TCDF in HEPG2 cells is visible as the darkest band in lane 2. No band having identical mobility is present in the other three lanes. The blot was deliberately overdeveloped to make certain there is no trace of CYP1A1 in the XPA fibroblasts. Microsomal proteins from: vehicle treated HEPG2 cells, lane 1: TCDF treated HEPG2 cells, lane 2; vehicle treated XPA fibroblasts, lane 3; TCDF treated XPA fibroblasts, cells, lane 4. The XPA fibroblasts did not show CYP1A1 expression induced by TCDF whereas the HEPG2 cells showed considerable induction of CYP1A1 expression as expected. Thus, the antibody for rat CYP1A1 cross reacts with similar determinants on human CYP1A1 as expected because the two proteins are highly homologous.

Figure 6:
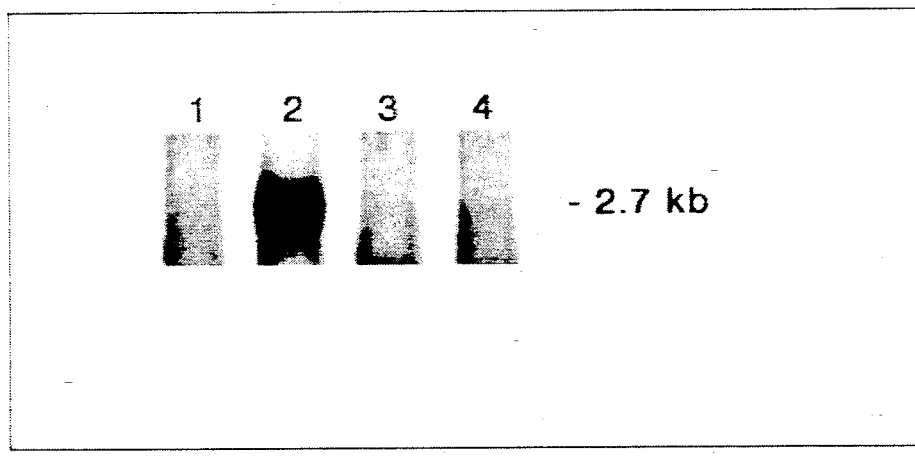
FIG. 6 shows induction of CYP1A1 mRNA detected by Northern blot in HEPG2 cells but not in XPA fibroblasts.

In addition, mRNAs from the induced and uninduced cells (both HEPG2 and XPA fibroblast) were analyzed by northern blot for CYP1A1 mRNA expression. FIG. 6 shows induction of CYP1A1 mRNA detected by northern blot in HEPG2 cells but not in XPA fibroblasts. Total RNA was prepared from cells treated concurrently with those of FIG. 1. The RNAs were fractionated by denaturing agarose gel electrophoresis, transferred to a modified nylon membrane and hybridized to a radiolabelled probe specific for human CYP-1A1. CYP1A1 hybridizing mRNAs are visible as an intense band in the RNA from TCDF-treated HEPG2 cells (lane 2) but in none of the others. The autoradiograph was deliberately overexposed to make certain there is no trace of CYP1A1 mRNA in the XPA fibroblasts. RNAs from: vehicle-treated HEPG2 cells, lane 1; TCDF-treated HEPG2 cells, lane 2; vehicle-treated XPA fibroblasts, lane 3; TCDF-treated XPA fibroblasts, lane 4.

Thus, only the induced HEPG2 cells showed any detectable CYP1A1 mRNA. It was concluded that the human fibroblast cells do not express CYP1A1 or CYP-2E1. Thus, they are suitable as recipients of P450 cDNA expression constructs.

In order to determine if the model system for assessing cytotoxicity and mutagenicity of metabolically activated xenobiotics will be useful, applicants chose to begin their studies with a paradigm of a xenobiotic that requires activation, benzo[a]pyrene, and its known bioactivator, CYP1A1.

Cloning and Expression of Human CYP1A1 Coding Sequences

The human CYP1A1 gene was isolated from a Charon 4A genomic library and characterized by restriction endonuclease mapping and DNA sequence analysis (30). Several overlapping sub-clones have been constructed spanning from approximately 6000 bp 5' of the transcription initiation site to just 3' of the polyadenylation site (FIG. 4). FIG. 4 is a partial map of the 5830 bp human CYP1A1 gene. The open boxes represent non-coding exon information and closed boxes represent coding exon information. The position of restriction endonuclease recognition sites are shown for BglII (B), BclI (C), EcoRI (E), HinDIII (H), TaqI (T) and XbaI (X). The information contained in various sub-clones is shown below the map. The BclI/EcoRI fragment containing CYP1A1 coding information cloned into expression vectors to be used is denoted by the broken line. A shuttle vector, pRNH63, was prepared for the expression of the CYP1A1 structural gene under the direction of the mouse mammary tumor virus (MMTV) LTR and harvey murine sarcoma virus (Ha-MuSV) enhancer. Cloning of information into the unique BamH1 site of pRNH63 results in expression from the MTV/HaMuSV promoter/enhancer with 3' processing being contributed by the bovine growth hormone polyadenylation signal. In addition, kanamycin/Geneticin resistance, expressed under the prokaryotic P1 and eukaryotic tk promoters, provides a means for selection.

For the expression of CYP1A1 information, a 2.0 kb BclI/BamHI fragment containing the entire coding information for the CYP1A1 protein was cloned into the BamHI site of pRNH63 and used to transfect the human breast tumor cell line, MCF-7. Several stable tranfectants were cloned. However, each exhibited an extremely slow growing phenotype suggesting that expression of the normally silent CYP1A1 gene under this relatively powerful promoter system was most likely toxic. Thus a less potent inducible promoter system is preferred for use with the present invention.

Choice of Inducible Promoter

An inducible promoter allows direct comparison of expression to chemicals in the same cell line under conditions which either do or do not induce expression of the P450 cDNA. Using the same cells ensures that there will be no variation in expression due to rearrangements in multi-copy transgenes or position effects which can be encountered when using several different transformants. The mouse metallothionein-I (MMT-I promoter is an inducible promoter with very low basal activity. As detailed below, its expression can be modulated by the concentration of metal ions in the media to give proportionately varied P450 levels. This is precisely what is needed to avoid the apparent toxicity of constitutive overproduction of CYP1A1 in human cells and will provide a means of correlating the level of P450 expression with mutagenic effect of a given dose of xenobiotic.

e. Studies Using the MMT-I Promoter

The MMT-I promoter was tested in a transient assay system in the XPA fibroblasts (GM4429) using chloramphenicol acetyl transferase (CAT) as a reporter. MMT-I promoter potency was compared to that of several other promoters. The basal and induced activities of the MMT-I were compared with the activity of the human adenosine deaminase (ADA) promoter, the herpes simplex virus-1 thymidine kinase (HSV-tk) promoter and two strong, viral promoters. SV40 early promoter and Rous Sarcoma Virus LTR. The basal activity of the MMT-I promoter was found to be very similar to the activities of both the ADA and the HSV-tk promoters. These are very weak constitutive promoters. The MMT-I promoter showed proportional inducibility with increasing $CdSO_4$ over the range of 1 to 5 $\mu M$. Maximum induction of 32-fold was achieved with an overnight incubation with 5 $\mu M$ $CdSO_4$ which was removed by washing the cells after the induction period. The cells seemed not to be adversely affected by this brief treatment and recovered well. Thus, the MMT-I promoter has very low activity in these cells but can be induced greatly by incubation with appropriate metals. If the low basal levels of the intact MMT-I promoter prove to be too high for use, a deletion mutant of the MMT-I promoter which has a 100-fold lower basal activity but is still inducible 20-fold by heavy metal can be used. This deletion mutant will surely give a basal activity which is low enough to avoid any problems associated with constitutive, high level expression of CYP1A1.

f. Synthesis and Testing of CYP1A1 Substrate

Figure 7:
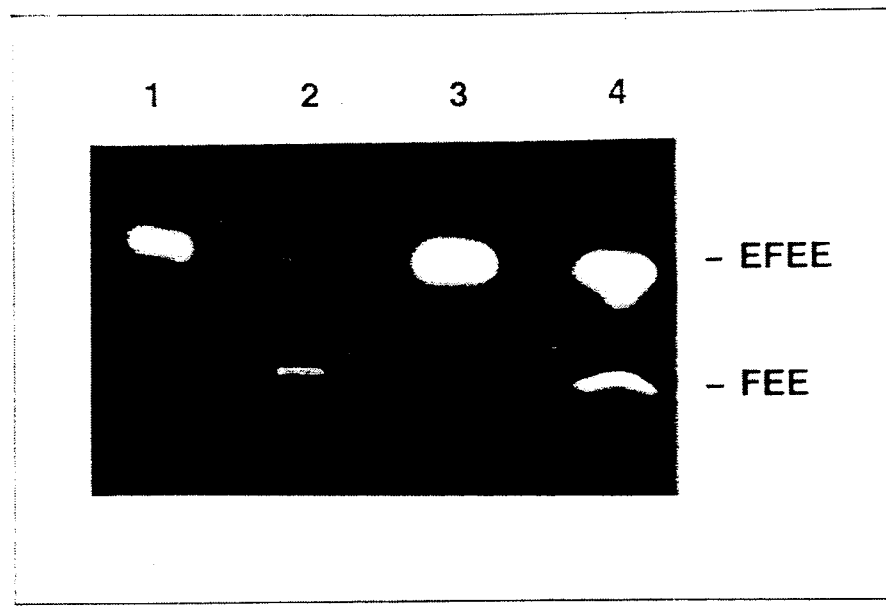
FIG. 7 shows test results of synthesized EFEE with HepG2 cells as a chromatograph developed with ethylacetate: benzene and visualized by illumination with long wave ultraviolet light.

Transformants will be screened for inducible CYP-1A1 activity by incubation of cells with ethoxy fluorescein ethyl ester (EFEE, see Experimental Methods). EFEE is not available commercially. Therefore, it is necessary to synthesize EFEE. The procedure of Miller (31) as modified by Salata (21) was used to prepare sufficient EFEE to screen several thousand cultures for CYP1A1 activity. The EFEE synthesized has been tested with HepG2 cells induced for CYP1A1 expression by TCDF exposure (FIG. 7).

HepG2 cells were plated in a 24-well multiwell plate and incubated until approximately 75% confluent. CYP1A1 was induced in the cells in half the wells (lanes 2 & 4) by addition of TCDF to 10 μM and the cells were incubated for 24 hours. The cells were washed three times with PBS, overlaid with 100 μl PBS containing EFEE at 500 nM (lanes 1 & 2) or 5 μM (lanes 3 & 4) and incubated for one hour. The PBS-EFEE from each well was withdrawn and acidified by addition of 10 μl 1N HCl. Thin layer chromatography was performed with 50 μl aliquots of the acidified samples. The chromatograph was developed with ethylacetate:benzene (3:1) and visualized by illumination with long wave UV. At lower doses of EFEE (500 nM), nearly all is converted to FEE by the HepG2 cells. At a higher dose (5 μM), only a portion of the EFEE is converted to FEE. Thus, applicants have successfully synthesized this critical reagent and demonstrated its usefulness in screening small scale cultures for inducible CYP1A1 activity both rapidly and easily.

g. Characterization of CYP1A1 Transformed Fibroblasts

Figure 8:
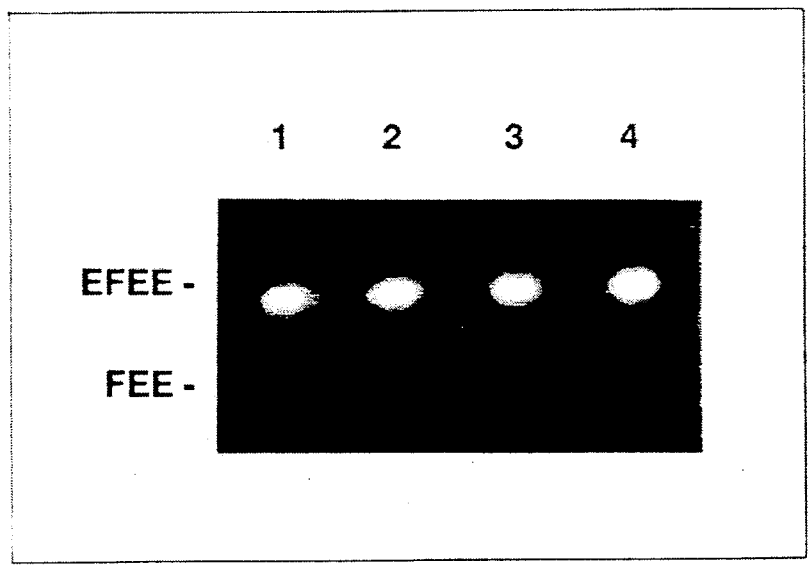
FIG. 8 is a chromatograph visualized by illumination with long wave ultraviolet light showing analysis of NEO+ transformants for CYP1A1 activity inducible by 5 $\mu$M $CdSO_4$.

DNA repair normal (GM0637) and XPA (GM4429 & GM4312) fibroblasts were co-tranfected with the dominant selectable marker pRSV-NEO and the CYP1A1 chimeric gene construct at three different ratios of DNAs as described in Experimental Methods. Several hundred colonies of NEO+ transformants were obtained from one XPA (GM4429 and the normal (GM0673) transfected fibroblasts by plating at low density and incubating in media containing G-418 (300 μg/ml). Twenty-three colonies were isolated and grown individualy in mass culture . Analysis for CYP-1A1 activity inducible by CdSO4 was performed utilizing the EFEE assay. One transformant (of 23 tested) was identified as having CYP1A1 activity inducible by 5 μM CdSO4 (FIG. 8).

Individual NEO+ transformant colonies were isolated and grown in mass culture. Cells were trypsinized and plated in duplicate in 24-well multi-well plates. When the cells were 75% confluent, the media was changed. One well of each pair received 0.5 ml normal media and the other received 0.5 ml media containing 5 μM CdSO4. After incubation overnight, the media was removed, the cells were washed with PBS and then overlaid with 100 μl PBS containing 2.5 μM·EFEE and incubated 1.5 hours at 37° C. The PBS-EFEE from each well was withdrawn and acidified by addition of 10 μl N HCl. Thin layer chromatography was performed with 50 μl aliquots of the acidified samples. The chromatograph was developed with ethylacetate:benzene (3:1) and visualized by illumination with long wave UV. Lanes 1 & 2 are clone 6C cells; lanes 3 & 4 are clone 4T cells. Lanes 1 & 3 are cells induced with 5 μM CdSO4. The transformant expressing CYP1A1 (clone 6C) was XPA (GM4429) cells transfected with a 10:1 ratio of CYP1A1:pRSV-NEO DNAs and is clone 6C. All other transformanants analyzed had no CYP1A1 activity (like clone 4T). The CYP1A1 activity inducible in clone 6C cells is considerably lower than that inducible by TCDF in HepG2 cells (FIG. 7). The CYP1A1 activity in uninduced clone 6C cells is undetectable. These data indicate that XPA fibroblasts transformed with a CYP1A1 chimeric gene construct that uses the mouse metallothionein-I promoter to drive transcription of the CYP1A1 sequences and that is inducible by incubation with 5 μM CdSO4 can be obtained.

The invention has been described in an illustrative manner, and it is to be understood that the terminology which has been used is intended to be in the nature of words of description rather than of limitation.

Obviously many modifications and variations of the present invention are possible in light of the above teachings. It is, therefore, to be understood that within the scope of the appended claims the invention may be practiced otherwise than as specifically described.

---

SEQUENCE LISTING ( 1 ) GENERAL INFORMATION:

( i i i ) NUMBER OF SEQUENCES: 2

( v i ) CURRENT APPLICATION DATA:
      ( A ) APPLICATION NUMBER:
      ( B ) FILING DATE:

( 2 ) INFORMATION FOR SEQ ID NO:1:

( i ) SEQUENCE CHARACTERISTICS:
      ( A ) LENGTH: 6387 base pairs
      ( B ) TYPE: nucleic acid
      ( C ) STRANDEDNESS: double
      ( D ) TOPOLOGY: circular ( i i ) MOLECULE TYPE: DNA (genomic)

( v i ) ORIGINAL SOURCE:
      ( A ) ORGANISM: Homo sapiens ( i x ) FEATURE:
      ( A ) NAME/KEY: exon
      ( B ) LOCATION: complement (2807..3631)

( i x ) FEATURE:
      ( A ) NAME/KEY: exon (B) LOCATION: complement (2125..2251)

(ix) FEATURE:
    (A) NAME/KEY: exon
    (B) LOCATION: complement (1948..2037)

(ix) FEATURE:
    (A) NAME/KEY: exon
    (B) LOCATION: complement (1733..1856)

(ix) FEATURE:
    (A) NAME/KEY: exon
    (B) LOCATION: complement (1501..1587)

(ix) FEATURE:
    (A) NAME/KEY: exon
    (B) LOCATION: complement (237..1308)

(ix) FEATURE:
    (A) NAME/KEY: promoter
    (B) LOCATION: complement (3638..3967)

(ix) FEATURE:
    (A) NAME/KEY: CDS
    (B) LOCATION: 4586..5446

(xi) SEQUENCE DESCRIPTION: SEQ ID NO:1:

```
GCGCCCAATA CGCAAACCGC CTCTCCCCGC GCGTTGGCCG ATTCATTAAT GCAGCTGGCA    60
CGACAGGTTT CCCGACTGGA AAGCGGGCAG TGAGCGCAAC GCAATTAATG TGAGTTAGCT   120
CACTCATTAG GCACCCCAGG CTTTACACTT TATGCTTCCG GCTCGTATGT TGTGTGGAAT   180
TGTGAGCGGA TAACAATTTC ACACAGGAAA CAGCTATGAC CATGATTACG AATTCGACAA   240
ACATTAAAAA TAGACATTTT ATTACAAGAG TGTAGAGAAG GGAGACCAAT AGAAGGTAAT   300
TGAAATACCC CCCCCTCACT CCAGCCCTAG TCCTGGTGCC TGGATATGTG CACTCCCTGT   360
GCGCTCTGAT CCCCGCAGAC ACAAGTCCCC AGCCCCTCCA GGACAGCAAT AAGGGTCTTA   420
CAAGGCCAGA AGGCAGCCCT GTTTGTTCCT GCCTGCAGGA AGGGCAGAGG AATGTGATGT   480
TCCCAGGAAC TGTGTCCTAG ACCCATAGGG TCAGATTGCT CAGCCTAGTT CAAGCAGTGA   540
GACTACCTCT GTGCCAGTAT CCTGGGCTGT CTCTTCCCTT CACTCTTGGC AGCTCCCAAT   600
TGTCAAAGAT TGGACAGGGT CCTGGTTTGG CTAGTTCTAA CTTGCTGAAG CCAGTCAGCA   660
CCCTCACAGA GCCAGCTAGG TACTGGGCCC AGGGGCTTCC AGAGAGTTCT TCAGAGCTTC   720
TCAGAGGCCT AAGGACCTCC TAACCCTAGC AGGCCTCCTG GCTCAAGCAC AACTTGGGAA   780
GGCTCCATCA GCATCTATGT GGCCCTGTTT TACCTGTTGT CTCTGGAGGG TGTGCAGAGG   840
CAAGTCCAGG GTAGGGGCAG GCAGGATCCC TTAGGCTTGC CCACAGCCCA GATAGCAAAA   900
CTGCAGCCAG ATCAGTGTCT ATGAGTTTCA GGCTGAATCT TAGACCACAT AGGCCAGCCT   960
GCTGGTCTGG CTGCCCAACC AGACCAGGTA GACAGAGTCT AGGCCTCAGG GCTCTCAAGC  1020
ACCTAAGAGC GCAGCTGCAT TTGGAAGTGC TCACAGCAGG CATGCTTCAT GGTTAGCCCA  1080
TAGATGGGGG TCATGTCCAC CTTCACGCCC AGTGGCACGC TGAATTCCAC CCGTTGCAGC  1140
AGGATAGCCA GGAAGAGAAA GACCTCCCAG CGGGCAATGG TCTCACCGAT ACACTTCCGC  1200
TTGCCCATGC CAAAGATAAT CACCTTCTCA CTTAACACCT TGTCGATAGC ACCATCAGGG  1260
GTGAGAAACC GTTCAGGTAG GAACTCAGAT GGGTTGACCC ATAGCTTCCT GTAACCAGAG  1320
GGAGACAGCT GAAGTGGCAG TTCAGGGCTC AGAAGTGTCA AGTGAGTGGA GCTCCAGCCC  1380
CAAAGGATAG AGGACAGGCA AGCAGCCCAT GGACAGGAGG ATCAATGCAA TGATTGTATT  1440
AATCATATAT AAGAGCTTAA GAGGGTGGAC CCAGCCTTTC CTCTGCATCT CTGAACTTAC  1500
TGGTCATGGT TGATCTGCCA CTGGTTTACA AAGACACAAC GCCCCTTGGG GATGTAAAAG  1560
CCTTTCAAAC TTGTGTCTCT TGTTGTGCTA GGGAGAAAGG AAGCTCAGTC AGGCTCAGGG  1620
```

```
CAACAGGCAA ATCTCCCTGT CTCCCATGCC GTGTCCCTCC CACTAACCCT AATCAGGTAT    1680
GTGGTCCGGA GTAAGATCAG TAACAGACAG CAGTGGCTCC ATGGGGCCTT ACCTGTGGGG    1740
GATGGTGAAG GGGACGAAGG AAGAGTGTCG GAAGGTCTCC AGGATGAAGG CCTCCATATA    1800
GGGCAGATGG GATCTGTCAG AGAGCCGGGG CCGCCGTGAC CTGCCAATCA CTGTGTCTGC    1860
AGAACACAGG GACAAGATGG ATGCAGGGGC TGCCTAGACC TGGCCAGACC CCTGGCACTG    1920
ACCCCTTTGA AGGGAGCCAC TACCTACCTA GCTCCTCTTG GATCTTTCTC TGTACCCTGG    1980
GGTTCATCAC CAAATACATG AGGCTCCAGG AGATAGCAGT TGTGACTGTG TCAAACCCTG    2040
GACAGGGTAG AACAGAAGAA GTTAGGCAGG CAGCAGCAGG TCAGGGCACT TGAGCACAGG    2100
AAGGACACAA TGGGGTAACC ATACCAGCTC CAAAGAGGTC CAAGACGATG TTAATGATCT    2160
TCTCATCTGA CAGCTGGACA TTGGCGTTCT CATCCAGCTG CTTCTCCTGA CAGTGCTCAA    2220
TCAGGCTGTC TGTGATGTCC CGGATGTGGC CCTTAGGTAG GGAAAGTCCA CAGGTGAGCA    2280
AGATCTCAAA CCCAGAGCTA CCTCTCCATC CAGGTCTGGT CCTTCACTAT TCCTAGCACA    2340
TTTGTTCTGG AGGTGATGCC CCCTGAGGCT GTTGTCCCAG CTTCTCTCTG CCTCTGCAAG    2400
GCTCTCTCCT ACTACCTTAG AATGCTGCTA GCCCCAACTC ATGGGACATT TGACACACAG    2460
CGTCTTGTAC TGTTATCATC TGGATGTGCT CTTTATCTTC TTTCTATTAT GAGGCCAGGA    2520
GATGAACTCT TTAACTCTTC CTGGCTCCCT CAGCAACTGC CCCAGGGTCC TGCATGTAAT    2580
GACTCTTCAG TGGCTATTGC TGTCTGTGGA AGCATGGAAG GGTTAGTCAA GATAAAGTTC    2640
TATTTCCCTG CCAAGGAAGA AGACTATTCC ACAACTGGCT TCAAGATCCC AGGTTGAAGC    2700
CTTCCTGAGA ACTTGCCAAG CCCCATGCAG TTCCTCTTAC CTTTGACCTC CCAGGCCCTG    2760
ATGCCATCTG CTTCCCACCA CCCACCTGCC TTTCCCCAGA CTGTACCTTC TCAAAGGTTT    2820
TGTAGTGCTC CTTGACCATC TTCTGCATGA AGCTGTAGAA CTTCTCATTC AGGTCCTTGA    2880
AGGCATTCAG GGAAGGGTTG GGTAGGTAGC GAAGAATAGG GATGAAGTCA GCTGGGTTTC    2940
CAGAGCCAAC CACCTCCCCG AAATTATTAT TCAGGTTGAC TAGGCTAAGC AGTTCTTGGT    3000
GGTTGTGGTC ATAGCGCCGG CCAAAGCAAA TGGCACAGAT GACATTGGTC ACTGATACCA    3060
CCACATACCT GTAGGGGTTA AAGTGCCCAG GCCCTGCCAT CAGCTCCTGC AACGTGCTTA    3120
TCAGGACCTC AGCCTCCTTG CTCACATGCT CTTCCAGGTA GCAGGAGGTT GAGGAGGCTG    3180
GGTCAGAGGC AATGGAGAAA CTTTTCAGGC CATTCTGGGC CAGGCGCCGG CGGGCAGCCC    3240
ACACTGGTCC AGAGTCTGGG CTGAAGGACA TGCTCTGACC ATTACTGATG AGGGTGAAGG    3300
TGTAGAGGTC GGGCCGGCCC TTGAAATCAT CGCCCTGCCG CACCAGGGCC TGCCGGATGG    3360
TGTCCAGGCC GCTCAGCACC ACCACGGGTG TGGAGCCAAT TCGGATCTGC AGCACGTCCC    3420
CATACTGCTG GCTCATCCTT GACAGTGCCA GGTGCGGGTT CTTTCCCAGG GTCAGCATGT    3480
GCCCAATCAG AGGCCAGCCC CATGGCCCTG GTGGATTCTT CAGGCCTTTG GGACCTGAG    3540
GTCTTGAGGC CCTGATTACC CAGAATACCA GACAGAAGAT GACAGAGGCC AGAAGAAACT    3600
CCGTGGCCGA CATGGAGATT GGGAAAAGCA TGATCTGGTG AAGCTGGAGC TACGGAGTAA    3660
GTGAGGAGAA GGTACTCAGG ACGTTGAAGT CGTGGTGACG CTTAGAGGAC AGCCTGCCCT    3720
CTTTATAGTC GTTGGACGAG TCCGGGCGCA AAGGGTTTGC ACCCAGCAGG CGGTTGCTCC    3780
AGCCCACGCA TAGTCACGCG CCCCGCGTCC TGGCAGAGCC GAGCGCACTT TTCGGGCGGA    3840
GTGCAGAGCT CCCTGGAGCG CCAGTGTGCA CAGCGGGCAC GCCCCTTTGG CACGACTGGC    3900
TCGGATAGGA CGACCCATGT GACGTGTGGA ACATCATGTC CCTATAGTGC TTTCCCCGAT    3960
ATTACGGGGG CGAGCTCGAA TTAGCTTGGC ACTGGCCGTC GTTTTACAAC GTCGTGACTG    4020
GGAAAACCCT GGCGTTACCC AACTTAATCG CCTTGCAGCA CATCCCCCTT TCGCCAGCTG    4080
```

```
GCGTAATAGC GAAGAGGCCC GCACCGATCG CCCTTCCCAA CAGTTGCGCA GCCTGAATGG       4140
CGAATGGCGC CTGATGCGGT ATTTTCTCCT TACGCATCTG TGCGGTATTT CACACCGCAT       4200
ATGGTGCACT CTCAGTACAA TCTGCTCTGA TGCCGCATAG TTAAGCCAGC CCCGACACCC       4260
GCCAACACCC GCTGACGCGC CCTGACGGGC TTGTCTGCTC CCGGCATCCG CTTACAGACA       4320
AGCTGTGACC GTCTCCGGGA GCTGCATGTG TCAGAGGTTT TCACCGTCAT CACCGAAACG       4380
CGCGAGACGA AAGGGCCTCG TGATACGCCT ATTTTTATAG GTTAATGTCA TGATAATAAT       4440
GGTTTCTTAG ACGTCAGGTG GCACTTTTCG GGGAAATGTG CGCGGAACCC CTATTTGTTT       4500
ATTTTTCTAA ATACATTCAA ATATGTATCC GCTCATGAGA CAATAACCCT GATAAATGCT       4560
TCAATAATAT TGAAAAAGGA AGAGT ATG AGT ATT CAA CAT TTC CGT GTC GCC          4612
                             Met Ser Ile Gln His Phe Arg Val Ala
                              1               5

CTT ATT CCC TTT TTT GCG GCA TTT TGC CTT CCT GTT TTT GCT CAC CCA          4660
Leu Ile Pro Phe Phe Ala Ala Phe Cys Leu Pro Val Phe Ala His Pro
10               15                  20                  25

GAA ACG CTG GTG AAA GTA AAA GAT GCT GAA GAT CAG TTG GGT GCA CGA          4708
Glu Thr Leu Val Lys Val Lys Asp Ala Glu Asp Gln Leu Gly Ala Arg
             30                  35                  40

GTG GGT TAC ATC GAA CTG GAT CTC AAC AGC GGT AAG ATC CTT GAG AGT          4756
Val Gly Tyr Ile Glu Leu Asp Leu Asn Ser Gly Lys Ile Leu Glu Ser
         45                  50                  55

TTT CGC CCC GAA GAA CGT TTT CCA ATG ATG AGC ACT TTT AAA GTT CTG          4804
Phe Arg Pro Glu Glu Arg Phe Pro Met Met Ser Thr Phe Lys Val Leu
     60                  65                  70

CTA TGT GGC GCG GTA TTA TCC CGT ATT GAC GCC GGG CAA GAG CAA CTC          4852
Leu Cys Gly Ala Val Leu Ser Arg Ile Asp Ala Gly Gln Glu Gln Leu
 75                  80                  85

GGT CGC CGC ATA CAC TAT TCT CAG AAT GAC TTG GTT GAG TAC TCA CCA          4900
Gly Arg Arg Ile His Tyr Ser Gln Asn Asp Leu Val Glu Tyr Ser Pro
 90                  95                 100                 105

GTC ACA GAA AAG CAT CTT ACG GAT GGC ATG ACA GTA AGA GAA TTA TGC          4948
Val Thr Glu Lys His Leu Thr Asp Gly Met Thr Val Arg Glu Leu Cys
                 110                 115                 120

AGT GCT GCC ATA ACC ATG AGT GAT AAC ACT GCG GCC AAC TTA CTT CTG          4996
Ser Ala Ala Ile Thr Met Ser Asp Asn Thr Ala Ala Asn Leu Leu Leu
             125                 130                 135

ACA ACG ATC GGA GGA CCG AAG GAG CTA ACC GCT TTT TTG CAC AAC ATG          5044
Thr Thr Ile Gly Gly Pro Lys Glu Leu Thr Ala Phe Leu His Asn Met
         140                 145                 150

GGG GAT CAT GTA ACT CGC CTT GAT CGT TGG GAA CCG GAG CTG AAT GAA          5092
Gly Asp His Val Thr Arg Leu Asp Arg Trp Glu Pro Glu Leu Asn Glu
     155                 160                 165

GCC ATA CCA AAC GAC GAG CGT GAC ACC ACG ATG CCT GTA GCA ATG GCA          5140
Ala Ile Pro Asn Asp Glu Arg Asp Thr Thr Met Pro Val Ala Met Ala
170                 175                 180                 185

ACA ACG TTG CGC AAA CTA TTA ACT GGC GAA CTA CTT ACT CTA GCT TCC          5188
Thr Thr Leu Arg Lys Leu Leu Thr Gly Glu Leu Leu Thr Leu Ala Ser
             190                 195                 200

CGG CAA CAA TTA ATA GAC TGG ATG GAG GCG GAT AAA GTT GCA GGA CCA          5236
Arg Gln Gln Leu Ile Asp Trp Met Glu Ala Asp Lys Val Ala Gly Pro
         205                 210                 215

CTT CTG CGC TCG GCC CTT CCG GCT GGC TGG TTT ATT GCT GAT AAA TCT          5284
Leu Leu Arg Ser Ala Leu Pro Ala Gly Trp Phe Ile Ala Asp Lys Ser
     220                 225                 230

GGA GCC GGT GAG CGT GGG TCT CGC GGT ATC ATT GCA GCA CTG GGG CCA          5332
Gly Ala Gly Glu Arg Gly Ser Arg Gly Ile Ile Ala Ala Leu Gly Pro
 235                 240                 245

GAT GGT AAG CCC TCC CGT ATC GTA GTT ATC TAC ACG ACG GGG AGT CAG          5380
```

|   |   |   |   |   |   |   |   |   |   |   |   |   |   |   |
|---|---|---|---|---|---|---|---|---|---|---|---|---|---|---|
| Asp | Gly | Lys | Pro | Ser | Arg | Ile | Val | Val | Ile | Tyr | Thr | Thr | Gly | Ser | Gln |
| 250 |  |  |  |  | 255 |  |  |  | 260 |  |  |  |  | 265 |

```
GCA ACT ATG GAT GAA CGA AAT AGA CAG ATC GCT GAG ATA GGT GCC TCA        5428
Ala Thr Met Asp Glu Arg Asn Arg Gln Ile Ala Glu Ile Gly Ala Ser
                270                 275                 280

CTG ATT AAG CAT TGG TAACTGTCAG ACCAAGTTTA CTCATATATA CTTTAGATTG        5483
Leu Ile Lys His Trp
            285

ATTTAAAACT TCATTTTTAA TTTAAAAGGA TCTAGGTGAA GATCCTTTTT GATAATCTCA      5543
TGACCAAAAT CCCTTAACGT GAGTTTTCGT TCCACTGAGC GTCAGACCCC GTAGAAAAGA      5603
TCAAAGGATC TTCTTGAGAT CCTTTTTTTC TGCGCGTAAT CTGCTGCTTG CAAACAAAAA      5663
AACCACCGCT ACCAGCGGTG GTTTGTTTGC CGGATCAAGA GCTACCAACT CTTTTTCCGA      5723
AGGTAACTGG CTTCAGCAGA GCGCAGATAC CAAATACTGT CCTTCTAGTG TAGCCGTAGT      5783
TAGGCCACCA CTTCAAGAAC TCTGTAGCAC CGCCTACATA CCTCGCTCTG CTAATCCTGT      5843
TACCAGTGGC TGCTGCCAGT GGCGATAAGT CGTGTCTTAC CGGGTTGGAC TCAAGACGAT      5903
AGTTACCGGA TAAGGCGCAG CGGTCGGGCT GAACGGGGGG TTCGTGCACA CAGCCCAGCT      5963
TGGAGCGAAC GACCTACACC GAACTGAGAT ACCTACAGCG TGAGCTATGA GAAAGCGCCA      6023
CGCTTCCCGA AGGGAGAAAG GCGGACAGGT ATCCGGTAAG CGGCAGGGTC GGAACAGGAG      6083
AGCGCACGAG GGAGCTTCCA GGGGGAAACG CCTGGTATCT TTATAGTCCT GTCGGGTTTC      6143
GCCACCTCTG ACTTGAGCGT CGATTTTTGT GATGCTCGTC AGGGGGGCGG AGCCTATGGA      6203
AAAACGCCAG CAACGCGGCC TTTTTACGGT TCCTGGCCTT TGCTGGCCT TTTGCTCACA       6263
TGTTCTTTCC TGCGTTATCC CCTGATTCTG TGGATAACCG TATTACCGCC TTTGAGTGAG      6323
CTGATACCGC TCGCCGCAGC CGAACGACCG AGCGCAGCGA GTCAGTGAGC GAGGAAGCGG      6383
AAGA                                                                   6387
```

( 2 ) INFORMATION FOR SEQ ID NO:2:

( i ) SEQUENCE CHARACTERISTICS:
        ( A ) LENGTH: 286 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Met | Ser | Ile | Gln | His | Phe | Arg | Val | Ala | Leu | Ile | Pro | Phe | Phe | Ala | Ala |
|---|---|---|---|---|---|---|---|---|---|---|---|---|---|---|---|
| 1 |  |  |  | 5 |  |  |  |  | 10 |  |  |  |  | 15 |  |
| Phe | Cys | Leu | Pro | Val | Phe | Ala | His | Pro | Glu | Thr | Leu | Val | Lys | Val | Lys |
|  |  |  | 20 |  |  |  |  | 25 |  |  |  |  | 30 |  |  |
| Asp | Ala | Glu | Asp | Gln | Leu | Gly | Ala | Arg | Val | Gly | Tyr | Ile | Glu | Leu | Asp |
|  |  | 35 |  |  |  |  | 40 |  |  |  |  | 45 |  |  |  |
| Leu | Asn | Ser | Gly | Lys | Ile | Leu | Glu | Ser | Phe | Arg | Pro | Glu | Glu | Arg | Phe |
|  | 50 |  |  |  |  | 55 |  |  |  |  | 60 |  |  |  |  |
| Pro | Met | Met | Ser | Thr | Phe | Lys | Val | Leu | Leu | Cys | Gly | Ala | Val | Leu | Ser |
| 65 |  |  |  |  | 70 |  |  |  |  | 75 |  |  |  |  | 80 |
| Arg | Ile | Asp | Ala | Gly | Gln | Glu | Gln | Leu | Gly | Arg | Arg | Ile | His | Tyr | Ser |
|  |  |  |  | 85 |  |  |  |  | 90 |  |  |  |  | 95 |  |
| Gln | Asn | Asp | Leu | Val | Glu | Tyr | Ser | Pro | Val | Thr | Glu | Lys | His | Leu | Thr |
|  |  |  | 100 |  |  |  |  | 105 |  |  |  |  | 110 |  |  |
| Asp | Gly | Met | Thr | Val | Arg | Glu | Leu | Cys | Ser | Ala | Ala | Ile | Thr | Met | Ser |
|  |  | 115 |  |  |  |  | 120 |  |  |  |  | 125 |  |  |  |
| Asp | Asn | Thr | Ala | Ala | Asn | Leu | Leu | Leu | Thr | Thr | Ile | Gly | Gly | Pro | Lys |
|  | 130 |  |  |  |  | 135 |  |  |  |  | 140 |  |  |  |  |

| | | | | | | | | | | | | | | |
|---|---|---|---|---|---|---|---|---|---|---|---|---|---|---|
| Glu | Leu | Thr | Ala | Phe | Leu | His | Asn | Met | Gly | Asp | His | Val | Thr | Arg | Leu |
| 145 | | | | | 150 | | | | | 155 | | | | | 160 |
| Asp | Arg | Trp | Glu | Pro | Glu | Leu | Asn | Glu | Ala | Ile | Pro | Asn | Asp | Glu | Arg |
| | | | | 165 | | | | | 170 | | | | | 175 | |
| Asp | Thr | Thr | Met | Pro | Val | Ala | Met | Ala | Thr | Thr | Leu | Arg | Lys | Leu | Leu |
| | | | 180 | | | | | 185 | | | | | 190 | | |
| Thr | Gly | Glu | Leu | Leu | Thr | Leu | Ala | Ser | Arg | Gln | Gln | Leu | Ile | Asp | Trp |
| | | 195 | | | | | 200 | | | | | 205 | | | |
| Met | Glu | Ala | Asp | Lys | Val | Ala | Gly | Pro | Leu | Leu | Arg | Ser | Ala | Leu | Pro |
| | 210 | | | | | 215 | | | | | 220 | | | | |
| Ala | Gly | Trp | Phe | Ile | Ala | Asp | Lys | Ser | Gly | Ala | Gly | Glu | Arg | Gly | Ser |
| 225 | | | | | 230 | | | | | 235 | | | | | 240 |
| Arg | Gly | Ile | Ile | Ala | Ala | Leu | Gly | Pro | Asp | Gly | Lys | Pro | Ser | Arg | Ile |
| | | | | 245 | | | | | 250 | | | | | 255 | |
| Val | Val | Ile | Tyr | Thr | Thr | Gly | Ser | Gln | Ala | Thr | Met | Asp | Glu | Arg | Asn |
| | | | 260 | | | | | 265 | | | | | 270 | | |
| Arg | Gln | Ile | Ala | Glu | Ile | Gly | Ala | Ser | Leu | Ile | Lys | His | Trp | | |
| | | 275 | | | | | 280 | | | | | 285 | | | |

LIST OF REFERENCES

1. Ames, B. N., P. Sims and P. L. Grover (1972) *Science* 176:47–49.
2. Ames, B. N., J. McCann and E. Yamasaki (1975) *Mutat Res* 31:347–364.
3. Doga, S., J. Doehmer, H. Glatt, H. Molders, P. Siegert, T. Friedberg, A. Siedel and F. Oesch (1990) *Molec. Pharmacol.* 37:608–613.
4. Davies, R. L., C. L. Crespi, K. Rudo, T. R. Turner and R. L. Langenbach (1989) *Carcinogenesis* 10:885–891.
5. Crespi, C. L., D. T. Steimel, T. Ayoama, H. V. Gelboin and F. J. Gonzalez (1990) *Molec. Carcinogenesis* 3:5–8.
6. Crespi, C. L., R. langenbach, K. Rudo, Y. T. Chen, and R. L. Davies (1990) *Carcinogenesis* 10:295–301.
6a. Thompson, Litt (1991) *Mutation Res* 47:213–219.
6b. Gonzalez, F. J. et al. (1991) *Mutation Res* 247:113–127.
7. Gonzalez, F. (1990) *Pharma Ther* 45:1–38.
8. Nebert, D. W., M. Adesnik, M. J. Coon et al., (1987) *DNA* 6:1–11.
9. Nebert D. W., D. R. Nelson, M. Adesnik, et al. (1989) *DNA* 8:1–13.
9a. Homer et al. (1982) *J. Mol and Appl. Gen.* 1:273–288.
Cleaver, J. E. (1968) *Nature* 218:652–656.
11. Cleaver, J. E. (1973) *Cancer Res* 33:362–369.
12. Cleaver, J. E. and D. Bootsma (1975) *Ann Rev Genet* 9:19–38.
13. Kleijer, W. J., P. H. M. Lohman, M. P. Mulder et al. (1970) *Mutat Res* 9:517–523.
14. Kraemer, K. H., H. G. Coon, R. A. Petinga, S. F. Barrett, A. E. Rahe and J. H. Robbins (1975) *Proc Natl Acad Sci (USA)* 72:59–63.
15. Bhor, V. A., C. A. Smith, D. Okamoto and P. C. Hanawalt (1985) *Cell* 40:359–369.
16. Thomas, D. C., A. G. Morton, V. A. Bohr and A. Sancar (1988) *Proc Natl Acad Sci (USA)* 85:3723–3727.
17. Govan, H. L., III, Y. Valles-Ayoub and J. Braun (1990) *Nucleic Acids Res* 18:3823–3830.
18. Baker, S. J., E. R. Fearon, J. M. Nigro, D. R. Hamilton, A. C. Preisinger, J. M. Jessup, P. vanTuinen, D. H. Ledbetter, D. F. Barker, Y. Nakamura, R. White and B. Vogelstein, *Science* 244:217–221.
19. Gorman, C., R. Padmanabhan, and B. H. Howard (1983) *Science* 221:551–553.
20. vanGurp, J. R., and O. Hankinson (1984) *Mol Cell Biol* 4:1597–1604.
21. Puga, A. B., Raychaudhuri, K. Salata, Y-H Zhang and D. W. Nebert (1990) *DNA Cell Biol* 9:425–436.
22. Klotz, A. V., J. J. Stegement and C. Walsh (1984) *Anal Biochem* 140:138–145.
23. Guengerich, F. P., G. A. Dannan, S. T. Wright, M. V. Martin, and L. S. Kaminsky (1982) *Biochemistry* 21 60–6030.
24. Pasanen, M., T. Taskinen, E. A. Sotaniemi, M. Kairaluoma, and O. Pelkonen (1988) *Pharmacol Toxicol* 62:311–317.
25. McLemore, T. L., S. Adelberg, M. C. Liu, N. A. McMahon, S. J. Yu, W.C>Hubbard, M. Czerwinski, T. G. Wood, R. Storeng, R. A. Lubet, J. C. Eggleston, M. R. Boyd, and R. N. Hines (1990) *J. Nat'l Cancer Inst* 82:1333–1339.
26. Lubet, R. A., R. W. Nims, R. T. Mayer, J. W. Cameron, and L. M. Schechtman (1985) *Mutat Res* 142:127–131.
27. Akeson, A. L., D. A. Wiginton, M. R. Dusing, J. C. States and J. J. Hutton (1988) *J Biol Chem* 263:1629–16296.
28. States, J. C., *Mechanisms and Consequences of DNA Damage Processing*, UCLA Symposia on Molecular and Cellular Biology, New Series, Vol. 83, E. friedberg and P. Hanawalt, eds., Alan R. Liss Inc. (1988), p. 307–311.
29. Dohmer, J., S. Dogra, T. Friedberg, S. Monier, M. Adesnik, H. Glatt and F. Oesch (1988) *Proc Natl Acad Sci (USA)* 85:5769–5773.
30. Ivensen, P. L., W. J. Heiger, E. Bresnick, and R. N. Hines (1987) *Arch Biochem Biophys* 256:397–401.
31. Miller, A. G. (1983) *Anal Biochem* 33:46–57.

What is claimed is:

1. A method of testing for mutagenicity of a chemical by exposing human fibroblast test cells normally not including any cytochrome P450 activity, the test cells being transformed to express cytochrome P450 enzymes through the human CYP1A1 gene to the chemical in vitro; intracellularly metabolizing the chemical into a mutagenic metabolite by oxidatively metabolizing the chemical within the fibroblasts through the intracellular cytochrome P450 mixed function oxidase enzymes expressed by said transformed fibroblasts; and detecting gene damage in the test cells as an indication of mutagenicity of the chemical.

2. A method as set forth in claim 1 wherein said step of intracellularly metabolizing is further defined as oxidatively metabolizing the chemical through intracellular cytochrome P450 mixed function oxidase enzymes.

3. A method as set forth in claim 1 further including the step of the cells expressing CYP1A1 activity, said oxidatively metabolizing step being further defined as metabolizing the chemical through the CYP1A1 enzymes expressed by the fibroblasts intracellularly.

4. A method as set forth in claim 1 wherein the cells are DNA repair deficient for providing cells sensitive to mutagenicity at low doses as compared to doses required for detectable mutagenicity in cells which are not DNA repair deficient.

5. A method as set forth in claim 1 further including the step of creating a first test group of cells capable of having the metabolic activity and control cells genetically equivalent the first test group of cells but having significantly less metabolic activity.

6. A method as set forth in claim 5 wherein said creating step is further defined as inducing expression of enzymes having the metabolic activity in the first test group.

7. A method as set forth in claim 6 wherein said inducing step is further defined as inducing expression of intracellular cytochrome P450 mixed function oxidase enzymes.

8. A method as set forth in claim 7 wherein the cells are fibroblasts transformed to express cytochrome P450 enzymes under control of the mouse metallothionein-1 promoter and existing in a metal containing media, said inducing step being further defined as modulating the metallion content of the media within ranges which are non-toxic to the cells to modulate the expression of the P450 enzyme activity.

9. A method as set forth in claim 8 wherein said modulating step is further defined as modulating the activity of CYP1A1 in human fibroblast cells under the control of the inducible mouse metallothionein-1 promoter.

10. A cell line for testing for mutagenicity of a chemical, said cell line consisting essentially of fibroblasts normally having no detectable cytochrome P450 mixed function oxidase enzyme activity, said fibroblasts being transformed with chimeric gene constructs containing cytochrome P450 coding sequences and having intracellular cytochrome P450 oxidative metabolizing activity.

11. A cell line as set forth in claim 10 wherein said constructs express CYP1A1 activity.

12. A cell line as set forth in claim 10 wherein said fibroblasts are XPA cells which are DNA repair deficient.

13. A cell line as set forth in claim 10 wherein said cells are human fibroblasts.

14. A cell line as set forth in claim 13 wherein said fibroblasts are xeroderma pigmentosum group A cells.

15. A method of making a cell line for testing mutagenicity of a chemical, said method comprising the step of transforming XPA cells which are of a DNA repair deficient human fibroblast cell line, to express cytochrome P450 enzyme activity intracellularly.

* * * * *